United States Patent
Ohtsubo

(10) Patent No.: US 11,744,745 B2
(45) Date of Patent: Sep. 5, 2023

(54) ABSORBENT ARTICLE AND METHOD AND APPARATUS FOR MANUFACTURING ABSORBENT ARTICLE

(71) Applicant: UNICHARM Corporation, Ehime (JP)

(72) Inventor: Toshifumi Ohtsubo, Kagawa (JP)

(73) Assignee: Unicharm Corporation, Ehime (JP)

( * ) Notice: Subject to any disclaimer, the term of this patent is extended or adjusted under 35 U.S.C. 154(b) by 186 days.

(21) Appl. No.: 16/807,847

(22) Filed: Mar. 3, 2020

(65) Prior Publication Data
US 2020/0197230 A1    Jun. 25, 2020

Related U.S. Application Data

(63) Continuation of application No. PCT/JP2018/033230, filed on Sep. 7, 2018.

(30) Foreign Application Priority Data

Nov. 7, 2017 (JP) ................................. 2017-214643
Nov. 7, 2017 (JP) ................................. 2017-214647

(51) Int. Cl.
*A61F 13/15* (2006.01)
*A61F 13/49* (2006.01)
(Continued)

(52) U.S. Cl.
CPC .. *A61F 13/15601* (2013.01); *A61F 13/15203* (2013.01); *A61F 13/15739* (2013.01);
(Continued)

(58) Field of Classification Search
CPC .......... A61F 13/15601; A61F 13/15739; A61F 13/15406; A61F 13/49019;
(Continued)

(56) References Cited

U.S. PATENT DOCUMENTS 9,011,404 B2 *  4/2015  Kobayashi .......... A61F 13/4902
                                                   604/385.27
10,751,228 B2 *  8/2020  Kurohara ................ A61F 13/49
(Continued)

FOREIGN PATENT DOCUMENTS

CN      101652117 A    2/2010
CN      103957852 A    7/2014
(Continued)

OTHER PUBLICATIONS

Extended European Search Report issued in corresponding European Application No. 18876441.9, dated Jun. 19, 2020 (7 pages).
(Continued)

*Primary Examiner* — George R Koch
*Assistant Examiner* — Christopher C Caillouet
(74) *Attorney, Agent, or Firm* — Osha Bergman Watanabe & Burton LLP

(57) ABSTRACT

A method for manufacturing an absorbent article that includes: a first sheet body that includes two first sheets and a first elastic string that is stretchable and contractible in a left-right direction; a second sheet body; and a first weld portion. The method includes: (a) placing the first elastic string in a stretched state where the first elastic string is stretched in the left-right direction between the first sheets disposed in a thickness direction intersecting the left-right direction; (b) causing the second sheet body to overlap with the first sheet body in the thickness direction; (c) releasing the stretched state to bring about a released state; and (d) welding one end portion of the first sheet body in the left-right direction and one end portion of the second sheet body in the left-right direction to each other, to form the first weld portion.

7 Claims, 11 Drawing Sheets

(51) Int. Cl.
  *B29C 65/08* (2006.01)
  *B29C 65/74* (2006.01)
  *B29C 65/00* (2006.01)
  B29L 31/48 (2006.01)

(52) U.S. Cl.
  CPC .. *A61F 13/15747* (2013.01); *A61F 13/15764* (2013.01); *A61F 13/15772* (2013.01); *A61F 13/4902* (2013.01); *A61F 13/49019* (2013.01); *B29C 65/08* (2013.01); *B29C 65/74* (2013.01); *B29C 66/344* (2013.01); *B29C 66/43* (2013.01); *B29C 66/7294* (2013.01); *A61F 2013/15406* (2013.01); *B29K 2995/0046* (2013.01); *B29L 2031/4878* (2013.01)

(58) Field of Classification Search
  CPC .......... A61F 13/15203; A61F 13/15747; A61F 13/15764; A61F 13/15772; A61F 13/4902; A61F 2013/15406; A61F 13/4963; A61F 13/15593; B29C 65/08; B29C 65/74; B29C 66/344; B29C 66/43; B29C 66/7294; B29K 2995/0046; B29L 2031/4878
  See application file for complete search history.

(56) References Cited

U.S. PATENT DOCUMENTS

| 2002/0058922 | A1 | 5/2002 | Skog |
| 2010/0112313 | A1 | 5/2010 | Nakakado |
| 2018/0169964 | A1* | 6/2018 | Schneider ........... A61F 13/4902 |
| 2019/0374404 | A1* | 12/2019 | Ninomiya .............. B32B 37/00 |

FOREIGN PATENT DOCUMENTS

| CN | 106061451 A | 10/2016 |
| JP | 2002505159 A | 2/2002 |
| JP | 2013013683 A | 1/2013 |
| JP | 6171120 B1 | 7/2017 |
| JP | 6549207 B2 | 7/2019 |
| TW | M473199 U | 3/2014 |
| WO | 2009/082277 A1 | 7/2009 |
| WO | 2017130785 A1 | 8/2017 |

OTHER PUBLICATIONS

International Search Report issued in corresponding International Application No. PCT/JP2018/033230, dated Nov. 20, 2018, with translation (5 pages).

Written Opinion issued in corresponding International Application No. PCT/JP2018/033230, dated Nov. 20, 2018 (4 pages).

Office Action issued in corresponding Gulf Cooperation Council Application No. GC 2018-36402 dated Aug. 29, 2020 (5 pages).

International Preliminary Report on Patentability issued in corresponding International Patent Application No. PCT/JP2018/033230, dated May 22, 2020 (7 pages).

Office Action issued in the counterpart Japanese Patent Application No. 2019-116176, dated Jul. 13, 2021 (4 pages).

Office Action issued in the counterpart Chinese Patent Application No. 201880064734.2, dated Jun. 22, 2021 (24 pages).

Decision of Refusal issued in the corresponding Japanese Patent Application No. 2019-116176, dated Feb. 15, 2022 (2 pages).

Office Action issued in corresponding Tawianese Application No. 11021105780 dated Nov. 10, 2021 (3 pages).

Office Action issued in corresponding Chinese Application No. 201880064734.2 dated Nov. 25, 2021 (14 pages).

* cited by examiner

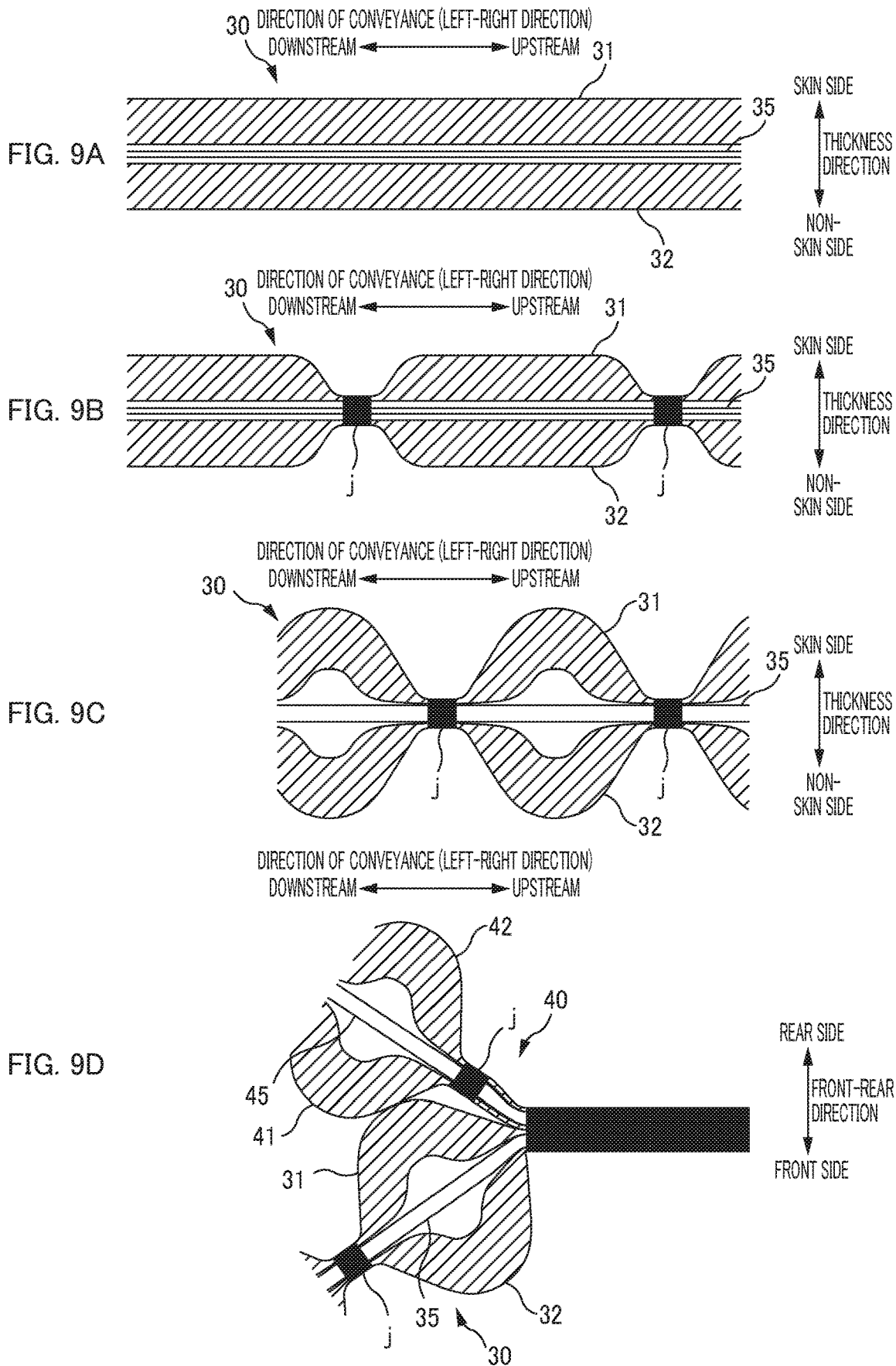

ABSORBENT ARTICLE AND METHOD AND APPARATUS FOR MANUFACTURING ABSORBENT ARTICLE

CROSS-REFERENCE TO RELATED APPLICATIONS

This application is based on and claims priority under 35 U.S.C. § 119 to Japanese Patent Application No. 2017-214643 filed on Nov. 7, 2017, and Japanese Patent Application No. 2017-214647 filed on Nov. 7, 2017, the contents of which are incorporated herein by reference.

TECHNICAL FIELD

The present invention generally relates to an absorbent article and a method and apparatus for manufacturing the absorbent article.

BACKGROUND

Absorbent articles such as a pull-on disposable diaper, a tape-type disposable diaper, and the like are known. For example, PTL 1 discloses a pull-on disposable diaper 1 in which both side edges of a front sheet member 2 and a back sheet member 3 are welded to form a pair of side seal portions S, thereby forming a waist opening W and a pair of leg openings LO, LO are formed.

PATENT LITERATURE

[PTL 1] Japanese Patent Application Publication No. 2013-13683

However, when a force is applied in a direction along elastic members 7 of the front sheet member 2 and the back sheet member 3 while the pull-on disposable diaper 1 of PTL 1 is worn or when putting on the diaper 1, welding of the side seal portion S may be separated.

SUMMARY

One or more embodiments of the present invention strengthen welding and bonding between members of an absorbent article and provide an absorbent article in which welding and bonding between members is strengthen.

One or more embodiments of the present invention provide a method for manufacturing an absorbent article including a first member (first sheet body), a second member (second sheet body), and a weld portion where the first member and the second member are welded to each other, the first member including two sheet members (sheets) having at least one nonwoven fabric, and an elastic member (elastic string) stretchably contractible in a left-right direction, the second member having a nonwoven fabric, the method comprising: an elastic member placing process of placing the elastic member in a stretched state between the two sheet members in a thickness direction intersecting the left-right direction of the first member, the stretched state being a state in which the elastic member is stretched in the left-right direction; an overlapping process of causing the second member to overlap with the first member in the thickness direction; a releasing process of releasing the stretched state to bring about a released state; and a welding process of welding one end portion in the left-right direction of the first member and one end portion in the left-right direction of the second member to each other, to form the weld portion, the welding process being performed in the released state after the releasing process.

Further, an absorbent article having an up-down direction, a left-right direction, and a thickness direction orthogonal to the up-down direction and the left-right direction, the absorbent article comprising: a first member including two first sheet members having at least one nonwoven fabric, and a first elastic member stretchably contractible in the left-right direction; a second member including two second sheet members having at least one nonwoven fabric, and a second elastic member stretchably contractible in the left-right direction; and a weld portion where end portions of the first member and the second member positioned on a same side in the left-right direction are welded and bonded to each other, the absorbent article further comprising, on each side in the left-right direction, a weld region overlapping with the weld portion, and an adjacent region adjacent to the weld region from an inner side, and a sum of a basis weight of the nonwoven fabric of the first member and a basis weight of the nonwoven fabric of the second member being greater in the weld region than the sum in the adjacent region, in a stretched state in which the first member and the second member are stretched along the left-right direction.

Other features of the present invention will become apparent from the description in the present specification and the accompanying drawings.

According to the method for manufacturing the absorbent article described above, welding is performed after stretch of the elastic member is released. Thus, it is possible to increase a basis weight of nonwoven fabric of the first member in the weld portion, thereby being able to further strengthen welding between the first member and the second member in the weld portion.

In such an absorbent article, since the basis weights of nonwoven fabric of the first member and the second member in the weld portion are great, it is possible to further strengthen welding between the first member and the second member in the weld portion.

BRIEF DESCRIPTION OF THE DRAWINGS

FIG. 9A is a schematic diagram for describing a cross section taken along a line a-a of FIG. 8A.

FIG. 9B is a schematic diagram for describing a cross section taken along a line b-b of FIG. 8B.

FIG. 9C is a schematic diagram for describing a cross section taken along a line c-c of FIG. 8C.

FIG. 9D is a schematic diagram for describing a cross section taken along a line d-d of FIG. 8D.

DETAILED DESCRIPTION OF EMBODIMENTS

Figure 1:
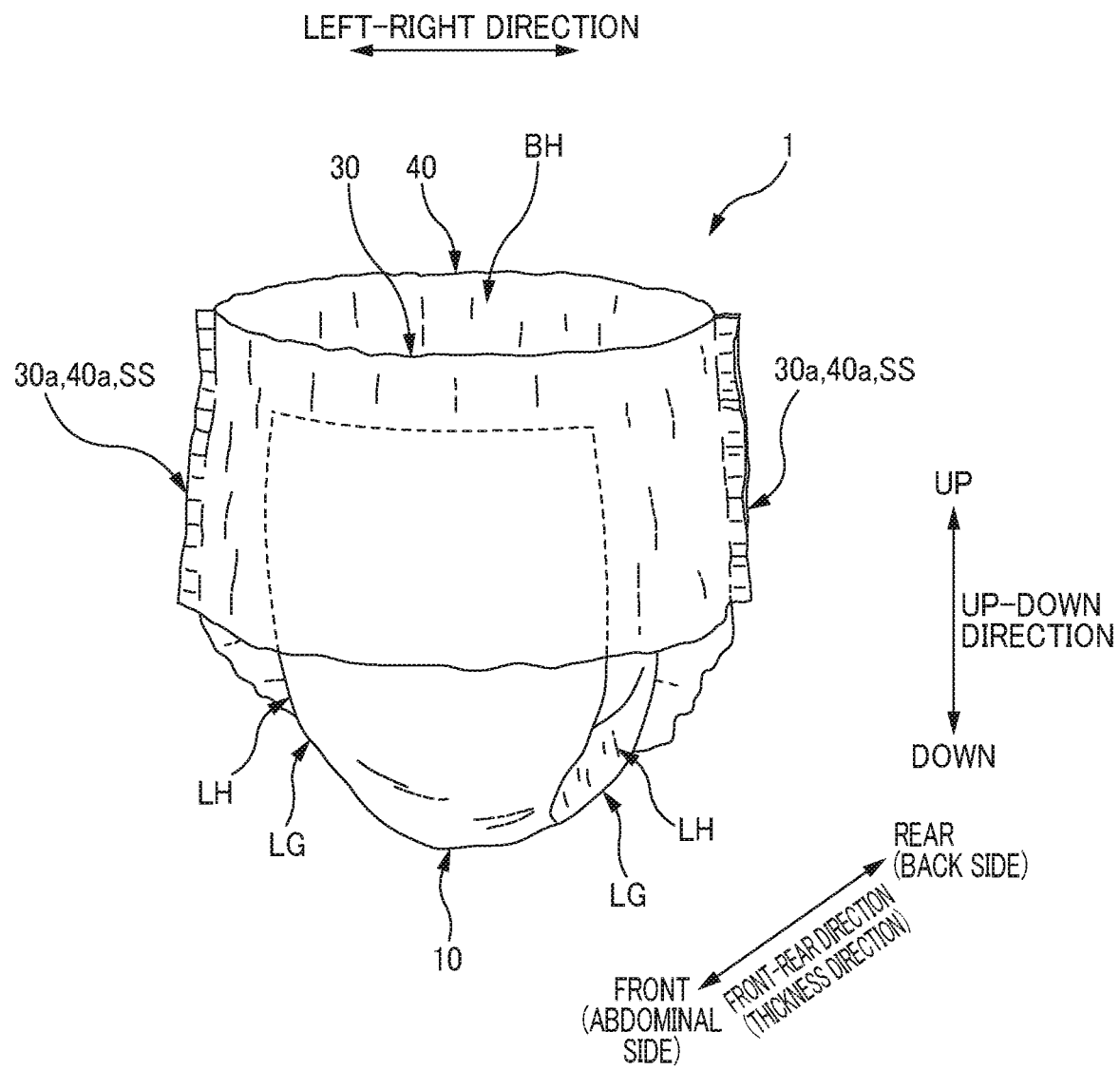
FIG. 1 is a schematic perspective view illustrating a pull-on disposable diaper 1 according to one or more embodiments.

At least following matter will become clear from the descriptions of the present specification with reference to the accompanying drawings.

A method for manufacturing an absorbent article including a first member, a second member, and a weld portion where the first member and the second member are welded to each other, the first member including two sheet members having at least one nonwoven fabric, and an elastic member stretchably contractible in a left-right direction, the second member having a nonwoven fabric, the method comprising: an elastic member placing process of placing the elastic member in a stretched state between the two sheet members in a thickness direction intersecting the left-right direction of the first member, the stretched state being a state in which the elastic member is stretched in the left-right direction; an overlapping process of causing the second member to overlap with the first member in the thickness direction; a releasing process of releasing the stretched state to bring about a released state; and a welding process of welding one end portion in the left-right direction of the first member and one end portion in the left-right direction of the second member to each other, to form the weld portion, the welding process being performed in the released state after the releasing process.

According to the method for manufacturing the absorbent article described above, welding is performed after stretch of the elastic member is released, so that a basis weight of the nonwoven fabric of the first member in the weld portion can be increased. Accordingly, it is possible to further strengthen welding between the first member and the second member in the weld portion.

In such a method for manufacturing an absorbent article, in the releasing process, the elastic member may be released so as to be in a state between the stretched state and a natural state, and the sheet members are in a state in which a plurality of wrinkles is formed in the left-right direction.

According to the method for manufacturing the absorbent article described above, in the first member, welding in the welding process after the releasing process can be performed in a more accurate position, as compared to a case where the elastic member is in a perfectly natural state.

In such a method for manufacturing an absorbent article, the sheet members may be first sheet members, the elastic member is a first elastic member, and the second member includes two second sheet members having at least one nonwoven fabric, and a second elastic member stretchably contractible in the left-right direction.

According to the method for manufacturing the absorbent article described above, it is possible to further strengthen welding between the first member and the second member, thereby being able to further strengthen welding between the front waist section and the back waist section in the pull-on diaper.

In such a method for manufacturing an absorbent article, the method may further include a sheet welding process of forming a sheet weld portion for welding the first sheet members to each other, wherein the sheet welding process is performed before the overlapping process and after the elastic member placing process, the sheet welding process includes disposing the sheet weld portions at intervals from one end portion to another end portion in the left-right direction of the first sheet members, to form a weld line along the left-right direction, and forming at least two or more weld lines spaced apart at a predetermined interval in an up-down direction intersecting the left-right direction, the first elastic member is provided between the weld lines adjacent to each other in the up-down direction, and the predetermined interval is greater than a thickness of the first elastic member in the stretched state and is smaller than a thickness of the first elastic member in the natural state.

According to the method for manufacturing the absorbent article described above, it is not necessary to bond the elastic member with an adhesive, thereby being able to making the first member softer as compared to a case where the elastic member is bonded with the adhesive.

In such a method for manufacturing an absorbent article, the method may further include a cutting process of cutting the first members in a continuous state, to form the first members in a cutout state, after the welding process, wherein the first members are in a state continuous in the left-right direction in the elastic member placing process, the sheet welding process, the overlapping process, the releasing process, and the welding process, and the cutting process is performed while the stretched state is released.

According to the method for manufacturing the absorbent article described above, since the cutting process is performed while stretch of the elastic member is released, the elastic member becomes thicker than that in the stretched state. Thus, it is possible to easily maintain a fixed state using the sheet weld portions, thereby being able to reduce the possibility that the elastic member slips off from the sheet weld portions even when the first member is cut out. Further, since an elastic member contraction force is reduced, it is possible to reduce the possibility that the elastic member comes off from the fixation with the sheet weld portions after the first member is cut out.

In such a method for manufacturing an absorbent article, in the welding process, the weld portion may be formed in a position overlapping with at least one of the sheet weld portions in the thickness direction.

According to the method for manufacturing the absorbent article described above, it is possible to increase the basis weight of the nonwoven fabric of the first member in the weld portion when the weld portion is formed on wrinkles that are formed between the sheet weld portions adjacent to each other in the left-right direction. Accordingly, it is possible to further strengthen welding between the first member and the second member in the weld portion.

In such a method for manufacturing an absorbent article, in the welding process, the weld portion may be formed in a position overlapping with two or more sheet weld portions in the thickness direction.

According to the method for manufacturing the absorbent article described above, it is possible to reliably increase the basis weight of the nonwoven fabric of the first member in the weld portion when the weld portion is formed on wrinkles formed between the sheet weld portions adjacent to each other in the left-right direction. Accordingly, it is possible to further strengthen welding between the first member and the second member in the weld portion.

In such a method for manufacturing an absorbent article, a plurality of the weld portions may be disposed along the up-down direction, and an interval between the weld portions adjacent to each other in the up-down direction is greater than the predetermined interval.

According to the method for manufacturing the absorbent article described above, it is possible to reduce the possibility that the elastic member is broken by the weld portion, as compared to a case where the length between the weld portions adjacent to each other in the up-down direction is smaller than the length between the weld lines.

In such a method for manufacturing an absorbent article, a length in the left-right direction of the weld portion may be greater than a length in the left-right direction of the sheet weld portion.

According to the method for manufacturing the absorbent article described above, it is possible to more reliably increase the basis weight of the nonwoven fabric of the first member in the weld portion, as compared to a case where the length in the left-right direction of the weld portion is smaller than the length in the left-right direction of the sheet weld portion. Accordingly, it is possible to further strengthen welding between the first member and the second member in the weld portion.

In such a method for manufacturing an absorbent article, a plurality of the first elastic members is provided. A plurality of the weld portions is disposed along the up-down direction. An interval of the first elastic members adjacent to each other in the up-down direction is greater than a length in the up-down direction of the weld portion.

According to the method for manufacturing the absorbent article described above, it is possible to reduce the possibility that the first elastic member is broken by the weld portion.

An apparatus for manufacturing an absorbent article having a first member, a second member, and a weld portion where the first member and the second member are welded to each other, the first member including two sheet members having at least one nonwoven fabric, and an elastic member stretchably contractible in a left-right direction, the second member having a nonwoven fabric, the apparatus comprising: an elastic member placing unit configured to place the elastic member in a stretched state between the two sheet members in a thickness direction intersecting the left-right direction of the first member, the stretched state being a state in which the elastic member is stretched in the left-right direction; an overlapping unit configured to cause the second member to overlap with the first member in the thickness direction; a releasing unit configured to release the stretched state to bring about a released state; and a weld forming unit configured to weld one end portion in the left-right direction of the first member and one end portion in the left-right direction of the second member to each other, to form the weld portion, the weld forming unit being configured to form the weld portion in the released state, after the releasing unit releases stretch in the stretched state.

According to the apparatus for manufacturing the absorbent article described above, it is possible to increase the basis weight of the nonwoven fabric of the first member in the weld portion by releasing stretch of the elastic member and then performing welding. Accordingly, it is possible to further strengthen welding between the first member and the second member in the weld portion.

An absorbent article having an up-down direction, a left-right direction, and a thickness direction orthogonal to the up-down direction and the left-right direction, the absorbent article comprising: a first member including two first sheet members having at least one nonwoven fabric, and a first elastic member stretchably contractible in the left-right direction; a second member including two second sheet members having at least one nonwoven fabric, and a second elastic member stretchably contractible in the left-right direction; and a weld portion where end portions of the first member and the second member positioned on a same side in the left-right direction are welded and bonded to each other, the absorbent article further comprising, on each side in the left-right direction, a weld region overlapping with the weld portion, and an adjacent region adjacent to the weld region from an inner side, and a sum of a basis weight of the nonwoven fabric of the first member and a basis weight of the nonwoven fabric of the second member being greater in the weld region than the sum in the adjacent region, in a stretched state in which the first member and the second member are stretched along the left-right direction.

According to the absorbent article described above, since the basis weights of the nonwoven fabrics in the weld portions of the first member and the second member are large, it is possible to further strengthen welding between the first member and the second member in the weld portion.

In such a method for manufacturing an absorbent article, the first sheet members are welded to each other in sheet weld portions, the sheet weld portions are arranged at intervals from one end portion to another end portion in the left-right direction of the first sheet members, to form a weld line along the left-right direction, at least two or more weld lines are provided while being spaced apart at a predetermined interval in the up-down direction, the first elastic member is provided between the weld lines adjacent to each other in the up-down direction, and the predetermined interval is greater than a thickness of the first elastic member in the stretched state and is smaller than a thickness of the elastic member in a natural state.

According to the absorbent article described above, it is possible to further strengthen welding between the first member and the second member, with the weld portion in a region where the sheet weld portion is provided.

In such a method for manufacturing an absorbent article, the weld portion is provided in a position overlapping with at least one of the sheet weld portions in the thickness direction.

According to the absorbent article described above, it is possible to further strengthen welding between the first member and the second member in the weld portion, even when the weld portion is provided so as to overlap with the sheet weld portion in the thickness direction.

In such a method for manufacturing an absorbent article, the weld portion is provided in a position overlapping with two or more sheet weld portions in the thickness direction.

According to the absorbent article described above, it is possible to further strengthen welding between the first member and the second member in the weld portion, even when the weld portion is provided so as to overlap with two or more sheet weld portions in the thickness direction.

In such a method for manufacturing an absorbent article, a plurality of the weld portions is disposed along the up-down direction, and a length between the weld portions adjacent to each other in the up-down direction is greater than the predetermined interval.

According to the absorbent article described above, it is possible to reduce the possibility that the elastic member is broken by the weld portion, as compared to a case where the length between the weld portions adjacent to each other in the up-down direction is smaller than the length between the weld lines.

In such a method for manufacturing an absorbent article, a length in the left-right direction of the weld portion is greater than a length in the left-right direction of the sheet weld portion.

According to the absorbent article described above, it is possible to further strengthen welding between the first member and the second member in the weld portion, as compared to a case where the length in the left-right direction of the weld portion is smaller than the length in the left-right direction of the sheet weld portion.

In such a method for manufacturing an absorbent article, a plurality of the first elastic members is provided, a plurality of the weld portions is disposed along the up-down direction, and an interval of the first elastic members adjacent to each other in the up-down direction is greater than a length in the up-down direction of the weld portions adjacent to each other in the up-down direction.

According to the absorbent article described above, it is possible to reduce the possibility that the first elastic member is broken by the weld portion.

EXAMPLES

FIG. 1 is a schematic perspective view illustrating a pull-on disposable diaper 1. In one or more embodiments, a so-called three-piece type pull-on diaper 1 of FIG. 1 is employed as an example of the absorbent article. The pull-on disposable diaper of one or more embodiments may be used for either an infant or an adult.

<Basic Configuration of Pull-On Disposable Diaper 1>

Figure 2A:
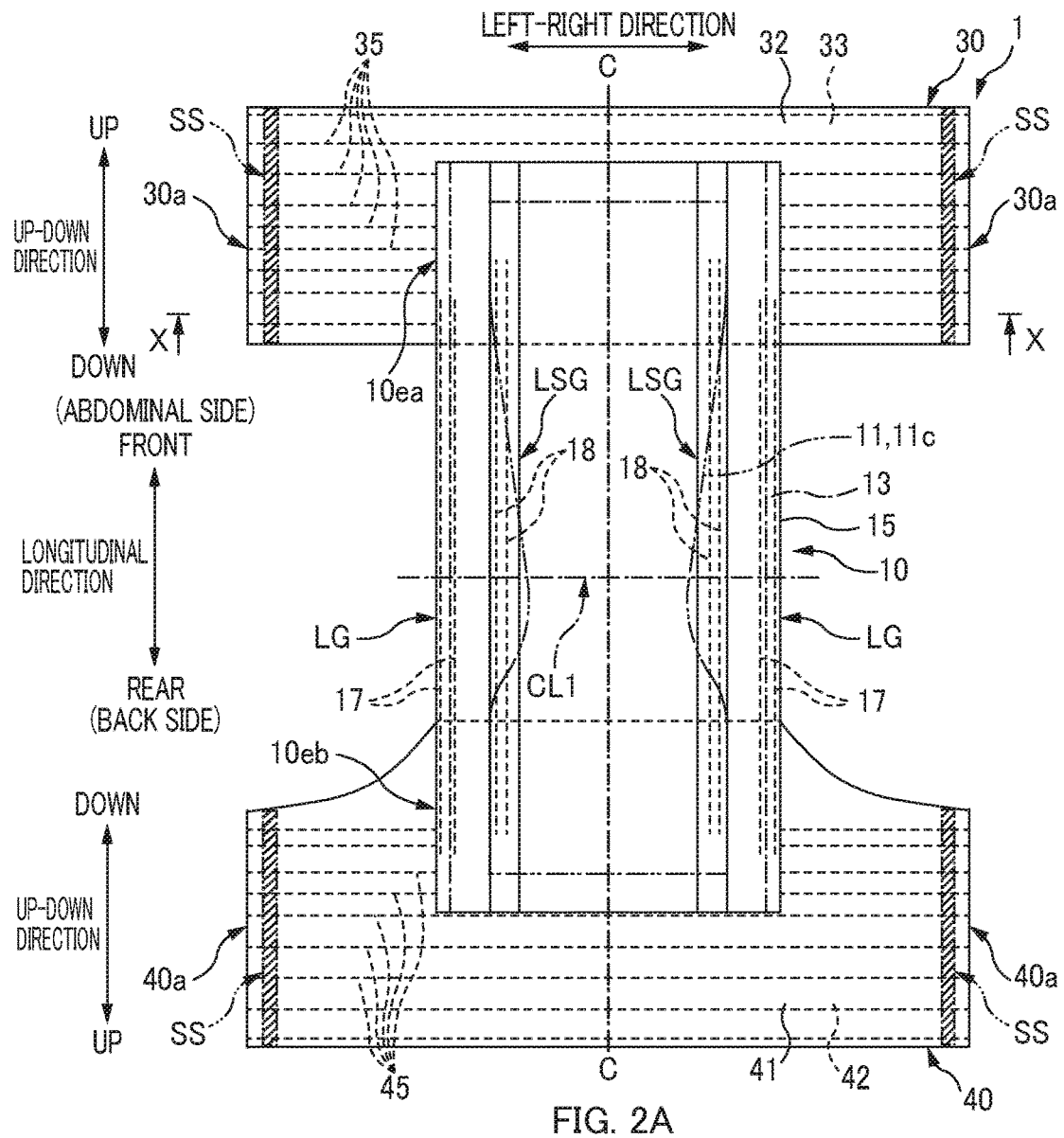
FIG. 2A is a schematic plan view illustrating the diaper 1 in an unfolded and stretched state as seen from a skin side according to one or more embodiments.
Figure 2B:
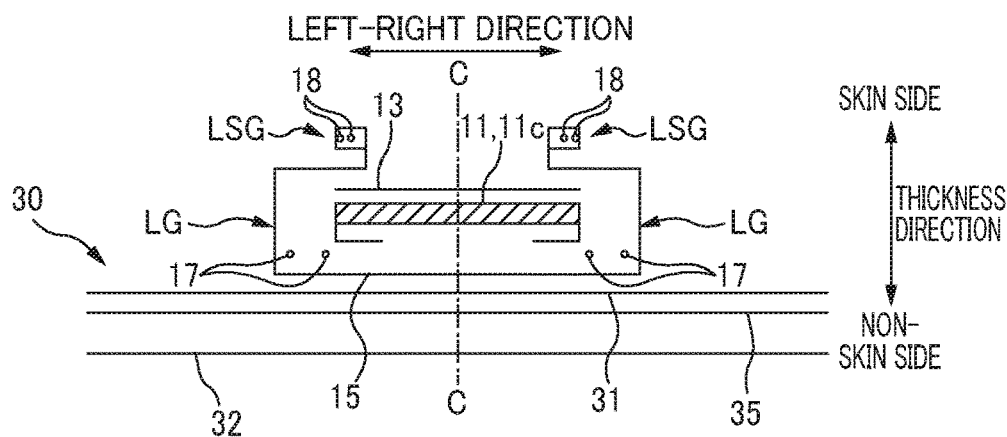
FIG. 2B is a schematic cross-sectional view taken along a line X-X of FIG. 2A.
Figure 3:
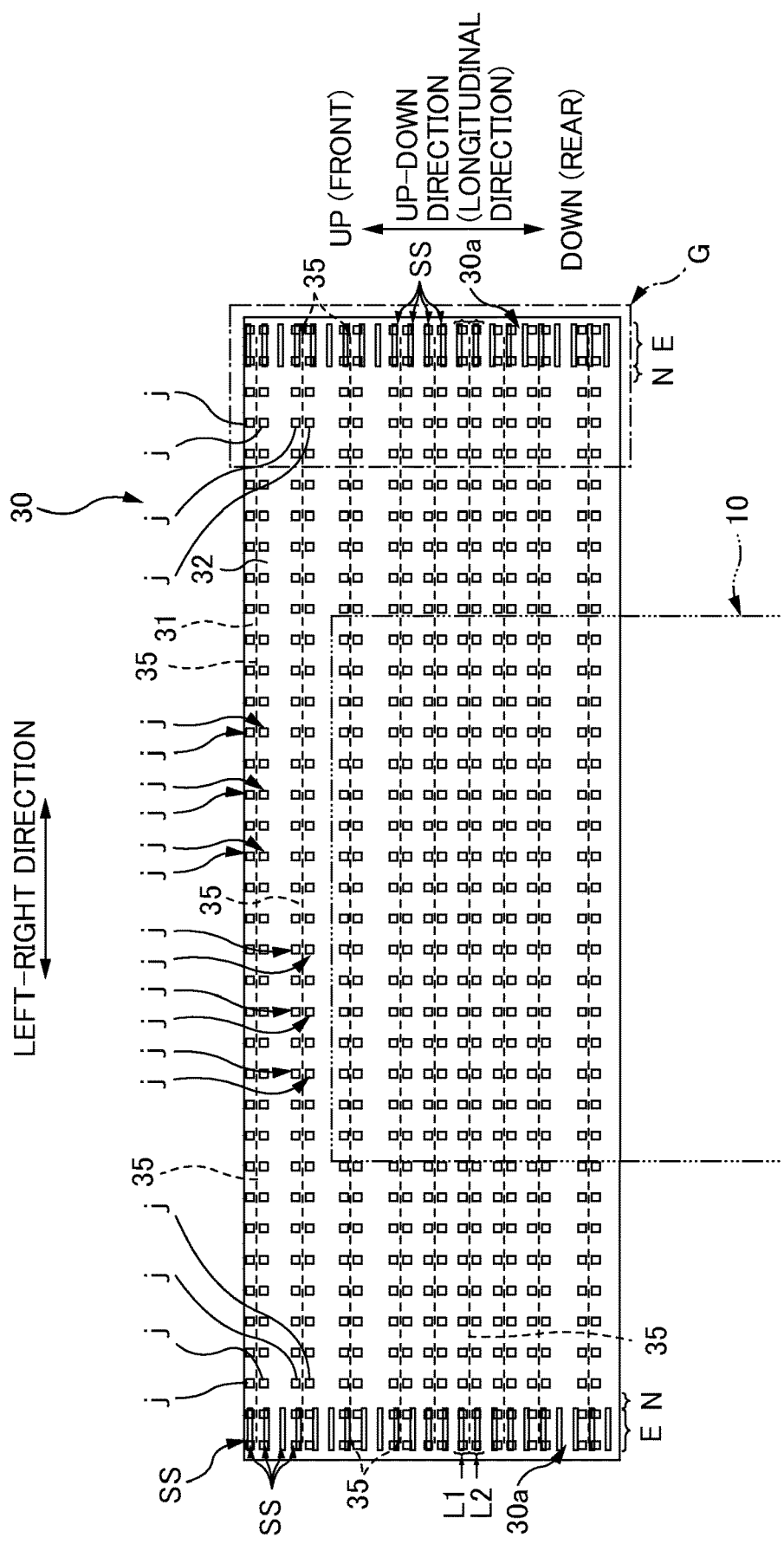
FIG. 3 is a schematic plan view illustrating a front member 30 in an unfolded and stretched state as seen from a non-skin side according to one or more embodiments.

FIG. 2A is a schematic plan view illustrating the diaper 1 in an unfolded or stretched state as seen from the skin side. FIG. 2B is a schematic cross-sectional view taken along the line X-X of FIG. 2A. FIG. 3 is a schematic plan view illustrating the front member 30 in an unfolded or stretched state as seen from the non-skin side. The "unfolded state" refers to a state in which the diaper 1 is opened by separating a side portion (also referred to as an "end portion") 30a of the front member 30 (also referred to as a "first member") and a side portion (also referred to as an "end portion") 40a of the back member 40 (also referred to as a "second member") that are to be welded at both side portions of the diaper 1, so that the diaper 1 is entirely unfolded on a plane. The "stretched state" refers to a state in which the elastic members provided in the diaper 1 are stretched to such a degree that wrinkles of the diaper 1 are not visually recognized. Specifically, in the stretched state, the elastic members are stretched such that dimensions of members (such as the front member 30 described below and the like) of the diaper 1 match or are close to the dimensions of the members of their own. The line C-C of FIG. 2 indicates a center line in the left-right direction. In FIG. 2B, the adhesive is not illustrated intentionally for simplicity. In the following description, the configuration of the front member 30 is similar to the configuration of the back member 40.

As illustrated in FIG. 1, an up-down direction, a left-right direction, and a front-rear direction are defined for the pull-on diaper 1, and the diaper 1 has a waist opening BH and a pair of leg openings LH. In the up-down direction, the waist opening BH side is defined as an upper side, and a wearer's crotch side is defined as a lower side. The up-down direction of the diaper 1 in the state of FIG. 2A (unfolded or stretched state) is referred to as a "longitudinal direction".

One side of the longitudinal direction is referred to as "front", and the other side of the longitudinal direction is referred to as "back". In addition, a substantial center C10 side of the longitudinal direction is referred to as a "lower side". In the front-rear direction, a wearer's abdominal side is defined as a "front" side, and a wearer's dorsal side is defined as a "back" side. In addition, as illustrated in FIG. 2B, a thickness direction is defined in the diaper 1, so that a side coming in contact with the wearer in the thickness direction is defined as an "skin" side, and the opposite side is defined as an "non-skin" side.

The diaper 1 is a so-called three-piece type and has an absorbent main body 10, a front member 30, and a back member 40. The front member 30 and the back member 40 have a substantially rectangular shape as seen in a plan view, and their longitudinal directions are placed along the left-right direction. The front member 30 covers a wearer's front portion, and the back member 40 covers a wearer's back portion. The absorbent main body 10 has a substantially rectangular shape as seen in a plan view. The end portion 10ea of the front side and the end portion 10eb of the back side of the absorbent main body 10 overlap with the skin-side surfaces of the front member 30 and the back member 40, respectively.

As illustrated in the unfolded state of FIG. 2A, the diaper 1 has a horizontally symmetrical shape with respect to the center line C-C. The non-skin surfaces of the end portion 10ea of the front side and the end portion 10eb of the back side of the absorbent main body 10 are welded to the skin-side surfaces of the front member 30 and the back member 40 using an adhesive (not shown) or the like, and the absorbent main body 10 is folded in half from the unfolded state of FIG. 2A such that the front member 30 and the back member 40 face each other. Then, both side portions 30a in the left-right direction of the front member 30 and both side portions 40a in the left-right direction of the back member 40 are welded and bonded to each other with side weld portions SS, so that the diaper 1 is formed into a pants shape.

Each of the front member 30 and the back member 40 has two flexible sheet members such as nonwoven fabric (including a skin-side sheet member 31 and a non-skin-side sheet member 32, and a skin-side sheet member 41 and a non-skin-side sheet member 42) and a plurality of elastic strings (elastic members) 35 and 45 contractibly stretched in the left-right direction. A plurality of elastic strings 35 and 45 is arranged side by side at intervals in the up-down direction, and are fixed between a pair of sheet members (between 31 and 32 and between 41 and 42) while being stretched in the left-right direction. Accordingly, the front member 30 and the back member 40 are stretchable and contractible in the left-right direction to fit to a wearer's waist.

The absorbent main body 10 has a top sheet 13, an absorbent body 11, and a back sheet 15 bonded to each other using an adhesive such as a hotmelt. The top sheet 13 needs to be a liquid permeable sheet formed from hydrophilic air-through nonwoven fabric, spunbonded nonwoven fabric, or the like. The back sheet 15 may be a liquid non-permeable sheet formed from a polyethylene film, a polypropylene film, hydrophobic SMS nonwoven fabric, or the like. The top sheet 13 and the back sheet 15 are sized to cover the entire absorbent body 11.

The absorbent body 11 has a substantially rectangular shape as seen in a plan view and has an absorbent core 11c to absorb a liquid. The absorbent core 11c may be formed by shaping liquid absorbable fibers such as pulp fibers and may contain super-absorbent polymer (SAP) or the like.

In the absorbent main body 10, leg gathers LG provided in the right and left end portions to be stretchably contractible in the longitudinal direction, and barrier cuffs LSG provided on the skin side with respect to the absorbent body 11 as a leak-proof wall for preventing side leakage are formed with the back sheet 15. The leg gathers LG and the barrier cuffs LSG have elastic members 17 and 18, respectively, stretchable in the longitudinal direction (up-down direction).

The front member 30 has a skin-side sheet 31, an elastic member (first elastic member) 35, and a non-skin-side sheet 32 layered in this order in the thickness direction from the skin side and welded and bonded using a plurality of sheet weld portions j distributed across the up-down direction (longitudinal direction) and the left-right direction as illustrated in FIG. 3. Similarly, the back member 40 has a skin-side sheet 41, an elastic member (second elastic member) 45, and a non-skin-side sheet 42 layered in this order in the thickness direction from the skin side and welded and bonded using a plurality of sheet weld portions j distributed across the up-down direction and the left-right direction. Note that the elastic strings 35 and 45 are not bonded using the adhesive.

The skin-side sheets 31 and 41 and the non-skin-side sheets 32 and 42 are formed of nonwoven fabric, specifically, spunbonded nonwoven fabric. Alternatively, other types of nonwoven fabric such as SMS (spunbond/meltblown/spunbond) nonwoven fabric may also be employed without limitation thereto. In addition, although a single type of fiber of polypropylene (PP) of thermoplastic resin is employed as a fiber constituting the nonwoven fabric in one or more embodiments, it is not limited thereto. For example, a single fiber of any other type of thermoplastic resin such as polyethylene (PE) may be employed, or a composite fiber having a sheath-core structure such as PE and PP may be employed. In addition, both the skin-side sheets 31 and 41 and the non-skin-side sheets 32 and 42 may not be nonwoven fabric, and a soft sheet material other than the nonwoven fabric may be employed for any one of the skin-side sheets 31 and 41 or the non-skin-side sheets 32 and 42.

<<Side Weld Portion SS and Sheet Weld Portion j>>

Figure 4:
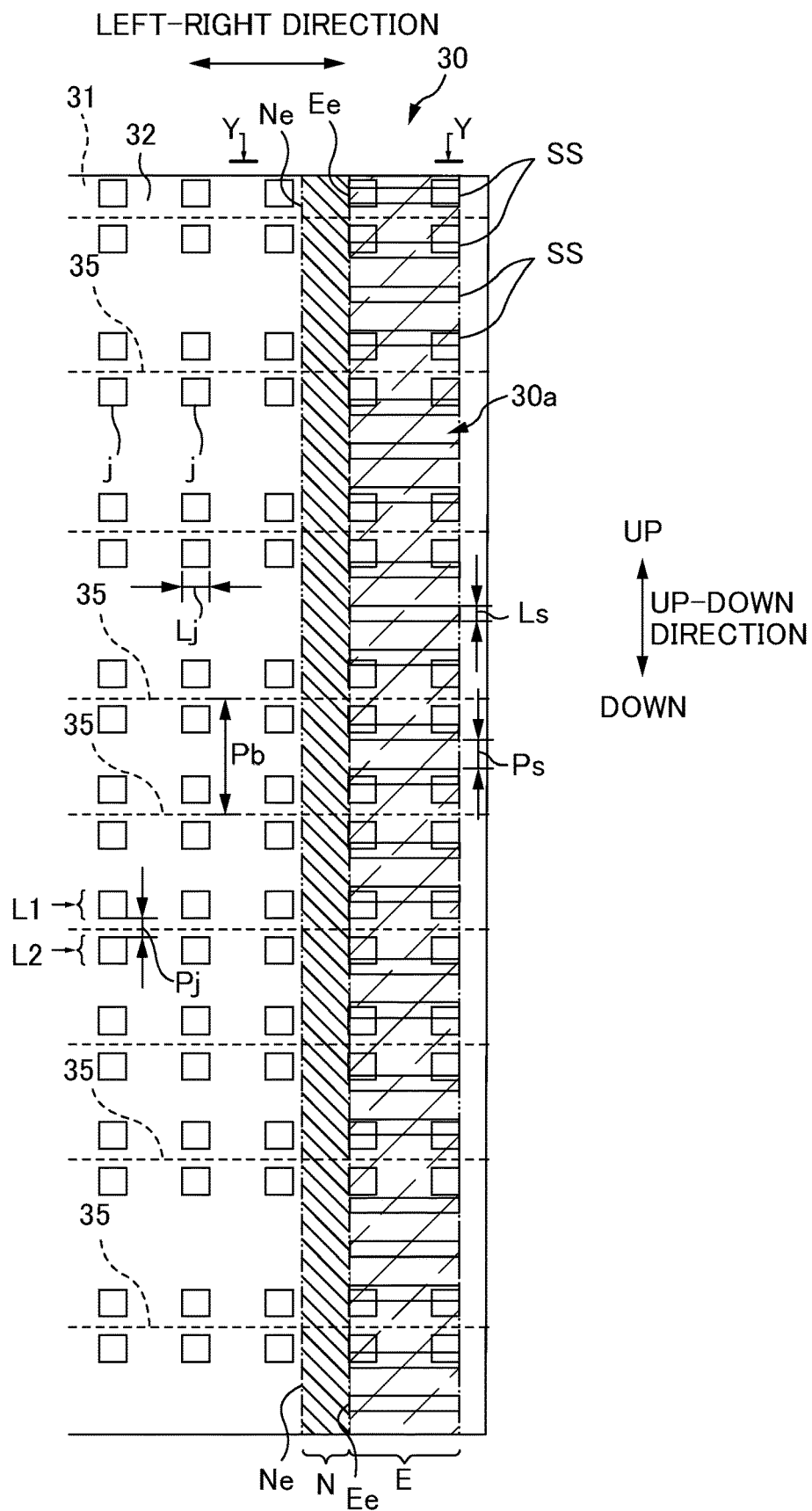
FIG. 4 is a schematic enlarged view illustrating a region G of FIG. 3.
Figure 5:
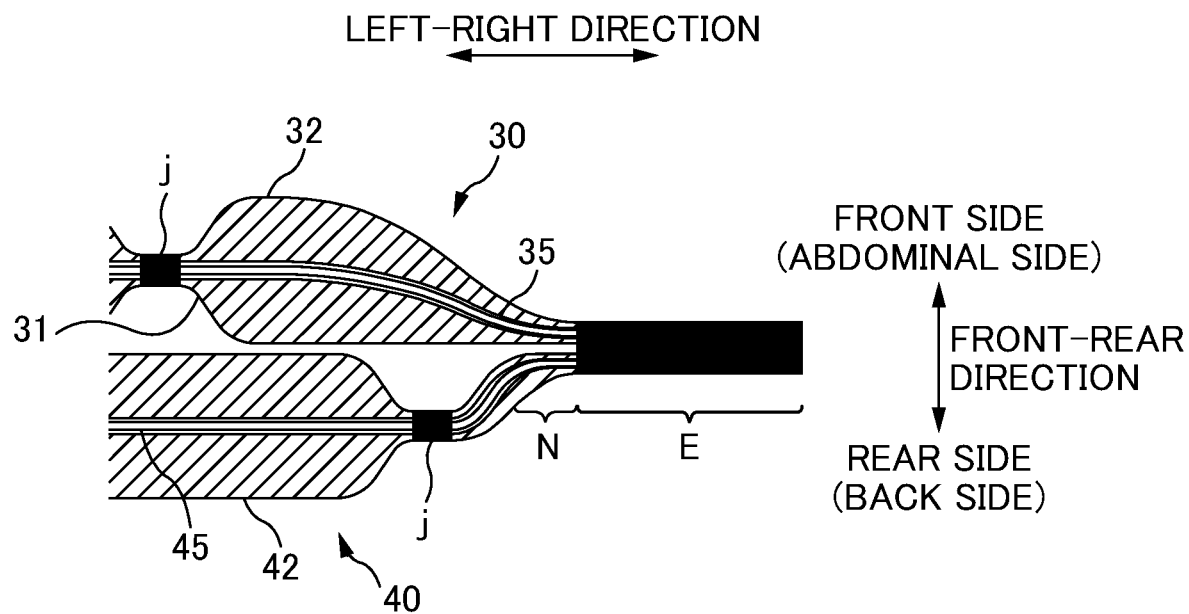
FIG. 5 is a schematic diagram for describing a cross section taken along a line Y-Y of FIG. 4.

The side weld portions SS and the sheet weld portions j will hereinafter be described in details. FIG. 4 is a schematic enlarged view illustrating a region G of FIG. 3. FIG. 5 is a schematic diagram for describing a cross section along the line Y-Y of FIG. 4. Although the side weld portions SS and the sheet weld portions j of the front member 30 will be mainly described for simplicity, the following description may also apply to the back member 40.

The end portions of the front member 30 and the back member 40 on the same side in the left-right direction are welded and fixed at the side weld portions SS. A plurality of side weld portions SS has substantially the same shape of a rectangular shape extending in the left-right direction and are arranged side by side at intervals in the up-down direction from the upper end portion to the lower end portion of the front member 30. The side weld portions SS are welded using ultrasonic waves and do not stretch/contract even when the elastic members 35 and 45 stretch or contract. A region where the side weld portions SS of the front member 30 and the back member 40 overlap in the left-right direction is referred to as a weld region E, and a region adjacent to the weld region E from the inside in the left-right direction is referred to as an adjacent region N. Specifically, the weld region E is a rectangular region extending from one end to the other end of the side weld portion SS in the left-right direction and extending from the upper end to the lower end of the front member 30 in the up-down direction. The adjacent region N is a rectangular region extending from the inner end Ee of the weld region E to the inner end Ne of the adjacent region N in the left-right direction and extending from the upper end to the lower end of each of the front member 30 and the back member 40 in the up-down direction. Note that a length in the left-right direction from the inner end Ee of the weld region E to the inner end Ne of the adjacent region N is set to 5 mm. In the diaper 1, since the front member 30 is smaller than the back member 40 in the up-down direction, the weld region E is defined as a region extending from the upper end to the lower end of the front member 30. However, if the back member 40 is shorter than the front member 30, a length in the up-down direction of the weld region E may be defined as a region extending from the upper end to the lower end of the back member 40. In FIG. 4, for simplicity, the weld region E is hatched with lines inclined downward to the left, and the adjacent region N is hatched with lines inclined downward to the right. Even when the elastic members 35 and 45 are stretched or contract, the weld region E is not easily affected by such stretch or contraction, and is not easily stretched or contracts.

In a stretched state in which the front member 30 and the back member 40 are stretched in the left-right direction, that is, while the elastic members 35 and 45 are stretched in the left-right direction, the sum of a basis weight of the nonwoven fabric of the front member 30 and a basis weight of the nonwoven fabric of the back member 40 in the weld region E is greater than the sum of a basis weight of the nonwoven fabric of the front member 30 and a basis weight of the nonwoven fabric of the back member 40 in the adjacent region N. The "basis weight of the nonwoven fabric" refers to a weight (kg/m2) of nonwoven fabric per unit area.

The sum of the basis weight of the nonwoven fabric of the front member 30 and the basis weight of the nonwoven fabric of the back member 40 may be measured and compared as follows. First, the sum of the basis weight of the nonwoven fabric of the front member 30 and the basis weight of the nonwoven fabric of the back member 40 in the weld region E is obtained by cutting out the weld region E from the diaper 1 in FIG. 1, measuring the weight (Ge) of the welding region E, and diving the weight of the weld region E by the area (Se) of the weld region E (Ge/Se). Note that, in the diaper 1, the area of the weld region E of the front member 30 is equal to the area of the welding region E of the back member 30, and the front member 30 and the back member 40 are integrated through welding. Accordingly, the sum of the basis weight of the nonwoven fabric of the front member 30 and the basis weight of the nonwoven fabric of the back member 40 in the weld region E can be obtained by Ge/Se. Meanwhile, the sum of the basis weight of the nonwoven fabric of the front member 30 and the basis weight of the nonwoven fabric of the back member 40 in the adjacent region N is obtained by cutting out the adjacent region N of the front member 30 and the adjacent region N of the back member from the diaper 1 of FIG. 1, and calculating the sum ((Gn30/Sn30)+(Gn40/Sn40)) of a value obtained by measuring the weight "Gn30" of the adjacent region N of the front member 30 and dividing the weight "Gn30" by the area "Sn30" of the adjacent region N of the front member 30 and a value obtained by measuring the weight "Gn40" of the adjacent region N of the back member 40 and dividing the weight "Gn40" by the area "Sn40" of the adjacent region N of the back member 40. As a result, it is possible to compare the sum (Ge/Se) of the basis weight of the nonwoven fabric of the front member 30 and the basis weight of the nonwoven fabric of the back member 40 in the weld region E and the sum ((Gn30/Sn30)+(Gn40/Sn40)) of the basis weight of the nonwoven fabric of the front member 30 and the basis weight of the nonwoven fabric of the back member 40 in the adjacent region N.

In FIG. 5, the sum of the basis weight of the nonwoven fabric of the front member 30 and the basis weight of the nonwoven fabric of the back member 40 is greater in the weld region E than that in the adjacent region N. However, the thickness in the front-rear direction of the weld region E is reduced through welding and bonding. In the welding and bonding, the nonwoven fabric is melted, and the melted parts of the nonwoven fabric are bonded to be fixed. Thus, as the amount of contained nonwoven fabric increases, the bonding strength is more improved. In the diaper 1, it is possible to improve the welding strength of the weld region E by setting the sum of the basis weight of the nonwoven fabric of the front member 30 and the basis weight of the nonwoven fabric of the back member 40 in the weld region E to be greater than the sum of the basis weight of the nonwoven fabric of the front member 30 and the basis weight of the nonwoven fabric of the back member 40 in the adjacent region N. As a result, it is possible to reduce the possibility that the front member 30 and the back member 40 is separated at the side portion 30a or 40a while the diaper 1 is worn or the like.

In some cases, the basis weight of the nonwoven fabric of the sheet members 31, 32, 41, and 42 of the front member 30 and the back member 40 may be set to be smaller in order to improve breathability of the front member 30 and the back member 40, reduce manufacturing costs, or improve texture. If the basis weight of the nonwoven fabric is set to be small across the entire area of the front member 30 and the back member 40, the amount of nonwoven fabric in the joining portion between the front member 30 and the back member 40 is reduced, so that the strength of bonding through welding may be lowered. In this regard, by setting the sum of the basis weight of the nonwoven fabric of the front member 30 and the basis weight of the nonwoven fabric of the back member 40 in the weld region E to be greater than the sum of the basis weight of the nonwoven fabric of the front member 30 and the basis weight of the nonwoven fabric of the back member 40 in the adjacent region N, it is possible to improve the welding strength between the front member 30 and the back member 40, reduce the possibility that the front member 30 and the back member 40 that are bonded are separated, and reduce the amount of the nonwoven fabric included in the front member 30 and the back member 40.

Similar to the side weld portion SS, the sheet weld portion j is also a portion welded using ultrasonic waves. A plurality of sheet weld portions j is used to weld the skin-side sheets 31 and 41 with the non-skin-side sheets 32 and 42 to each other, and the elastic strings 35 and 45 are arranged at predetermined positions to restrict movements of the elastic strings 35 and 45 in the up-down direction. The sheet weld portions j having a substantially square shape as seen in a plan view are arranged at intervals from one end portion to the other end portion in the left-right direction of the front member 30 to form weld lines L along the left-right direction. A plurality of weld lines L is spaced apart at predetermined intervals in the up-down direction. In this case, the elastic strings 35 are provided between the weld lines L adjacent to each other in the up-down direction, specifically, between the upper weld line L1 and the lower weld line L2 in FIG. 7, and the interval Pj is set to be greater than a thickness of the elastic string 35 when the front member 30 is in a stretched state and be smaller than the thickness of the elastic string 35 when the front member 30 is in a natural state, in one or more embodiments. Specifically, in FIG. 4, the elastic strings 35 are each provided between the upper weld line L1 and the lower weld line L2, and the interval (predetermined interval) Pj of the weld lines L adjacent to each other in the up-down direction is set to be substantially the same. In addition, the interval Pj is set to be greater than the thickness Ts (not shown) of the elastic string 35 in a stretched state and to be smaller than the thickness Tn (not shown) of the elastic string 35 in a natural state (Ts<Pj<Tn).

As a result, the sheet weld portions j provided in the up-down direction make it possible to reduce the possibility that the elastic string 35 excessively moves in the up-down direction. That is, since the thickness of the elastic string 35 in the stretched state is smaller than the interval Pj, the elastic string 35 is movable. However, as the elastic string 35 approaches its natural state and becomes thickened, the elastic string 35 is pressed in the up-down direction by the sheet weld portions j adjacent to each other in the up-down direction. Thus, it is possible to bring a state where a movement of the elastic string 35 is restricted. In this manner, by fixing the elastic string 35 to the weld portions j using stretch/contraction, it is possible to reduce the amount of the adhesive for fixing the elastic string 35 or not to use an adhesive. Thus, it is possible to improve texture by further softening the front member 30.

As illustrated in FIG. 4, in one or more embodiments, the side weld portion SS is provided at a position overlapping with at least one sheet weld portion j in the thickness direction. In addition, in one or more embodiments, the side weld portion SS is provided at a position overlapping with two or more sheet weld portions j in the thickness direction. Using such a side weld portion SS, it is possible to further strengthen bonding between the front waist section 30 and the back waist section 40.

As illustrated in FIG. 4, in one or more embodiments, the interval Ps of the side weld portions SS adjacent to each other in the up-down direction is greater than the interval Pj of the sheet weld portions j adjacent to each other in the up-down direction (Ps>Pj). Since the elastic string 35 is positioned between the sheet weld portions j adjacent to each other in the up-down direction, it is possible to reduce the possibility that the elastic string 35 is broken when forming the side weld portion SS, as compared to a case where the interval Ps of the side weld portions SS adjacent to each other in the up-down direction is smaller than the interval Pj of the sheet weld portions j adjacent to each other in the up-down direction.

Furthermore, in one or more embodiments, a length Ls in the left-right direction of the side weld portion SS is greater than a length Lj in the left-right direction of the sheet weld portion j (Ls>Lj). FIG. 4 illustrates the front member 30 in a stretched state, and the length Ls in the left-right direction of the side weld portion SS is greater than the length Lj in the left-right direction of the sheet weld portion j (Ls>Lj). However, since the side weld portions SS and the sheet weld portions j are not easily affected by contraction of the elastic string 35, the length Ls in the left-right direction of the side weld portion SS is greater than the length Lj in the left-right direction of the sheet weld portion j (Ls>Lj) even when the front member 30 is in a contracted state. Thus, it is possible to improve a welding strength of the side weld portion SS more than the welding strength in a case where the length Ls in the left-right direction of the side weld portion SS is smaller than the length Lj in the left-right direction of the sheet weld portion j (Ls<Lj).

Further, in one or more embodiments, the interval Pb of the elastic strings 35 adjacent to each other in the up-down direction is greater than the length Ls in the up-down direction of the side weld portion SS (Pb>Ls). Note that, when the elastic strings 35 adjacent to each other in the up-down direction are not at regular intervals of the intervals Pb as illustrated in FIG. 4 or the like, a length of the smallest interval Pb of the elastic strings 35 is greater than the length Ls in the up-down direction of the side weld portion SS, in one or more embodiments. As a result, it is possible reduce the possibility that the elastic string 35 and the side weld portion SS overlap in the thickness direction, thereby reducing the possibility that the elastic string 35 is broken by the side weld portion SS.

<Method for Manufacturing Pull-on Disposable Diaper 1>

The method and apparatus for manufacturing the absorbent article according to one or more embodiments are employed, for example, on a production line of the disposable diaper 1 as an exemplary absorbent article. Further, the absorbent article manufactured using the method and apparatus for manufacturing the absorbent article according to one or more embodiments may be employed for sanitary short-type napkins, tape-type disposable diapers, and pull-on disposable diapers for adults as well as infants.

Figure 6:
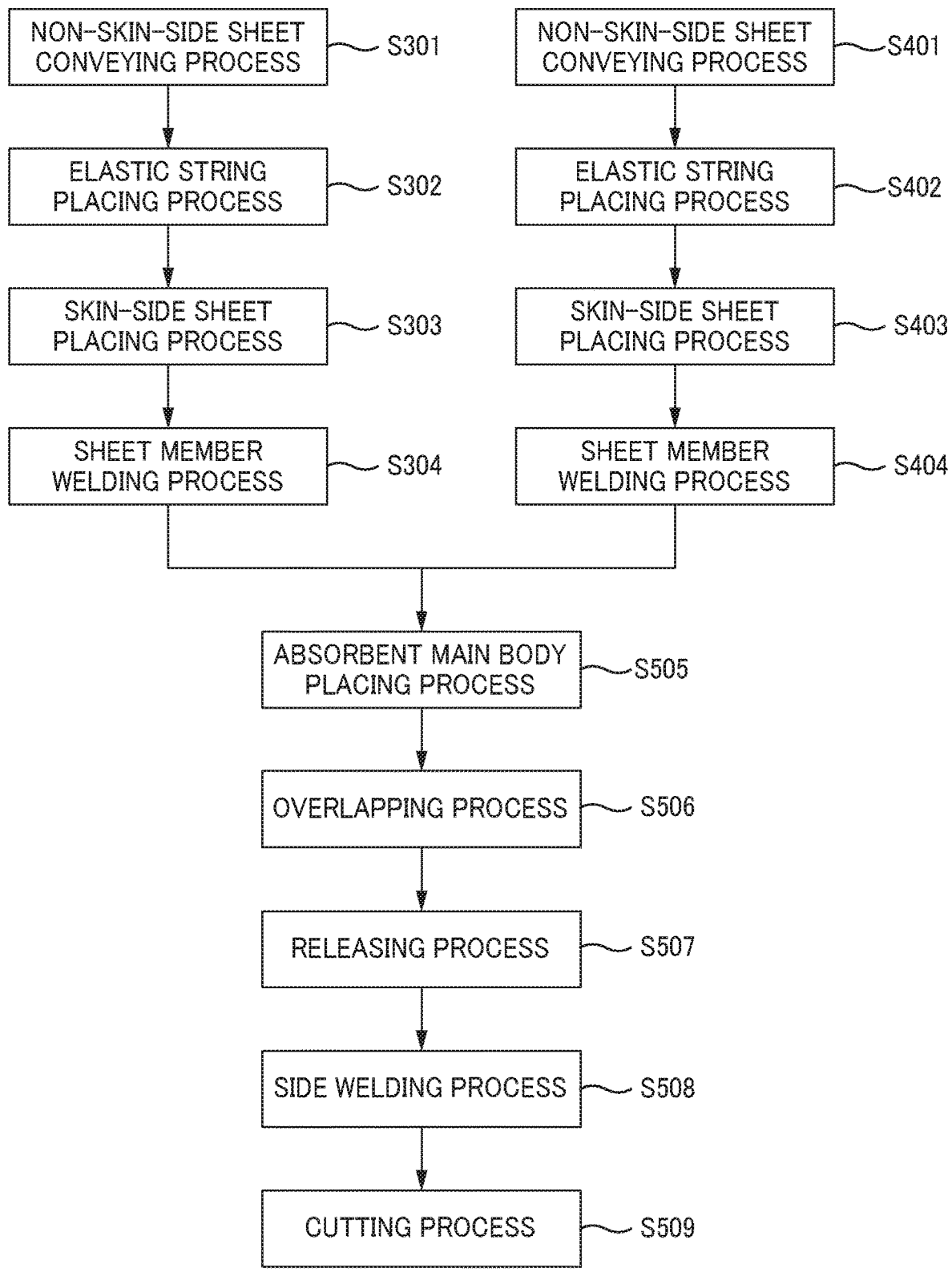
FIG. 6 is a flowchart illustrating a manufacturing process of the diaper 1 according to one or more embodiments.
Figure 7:
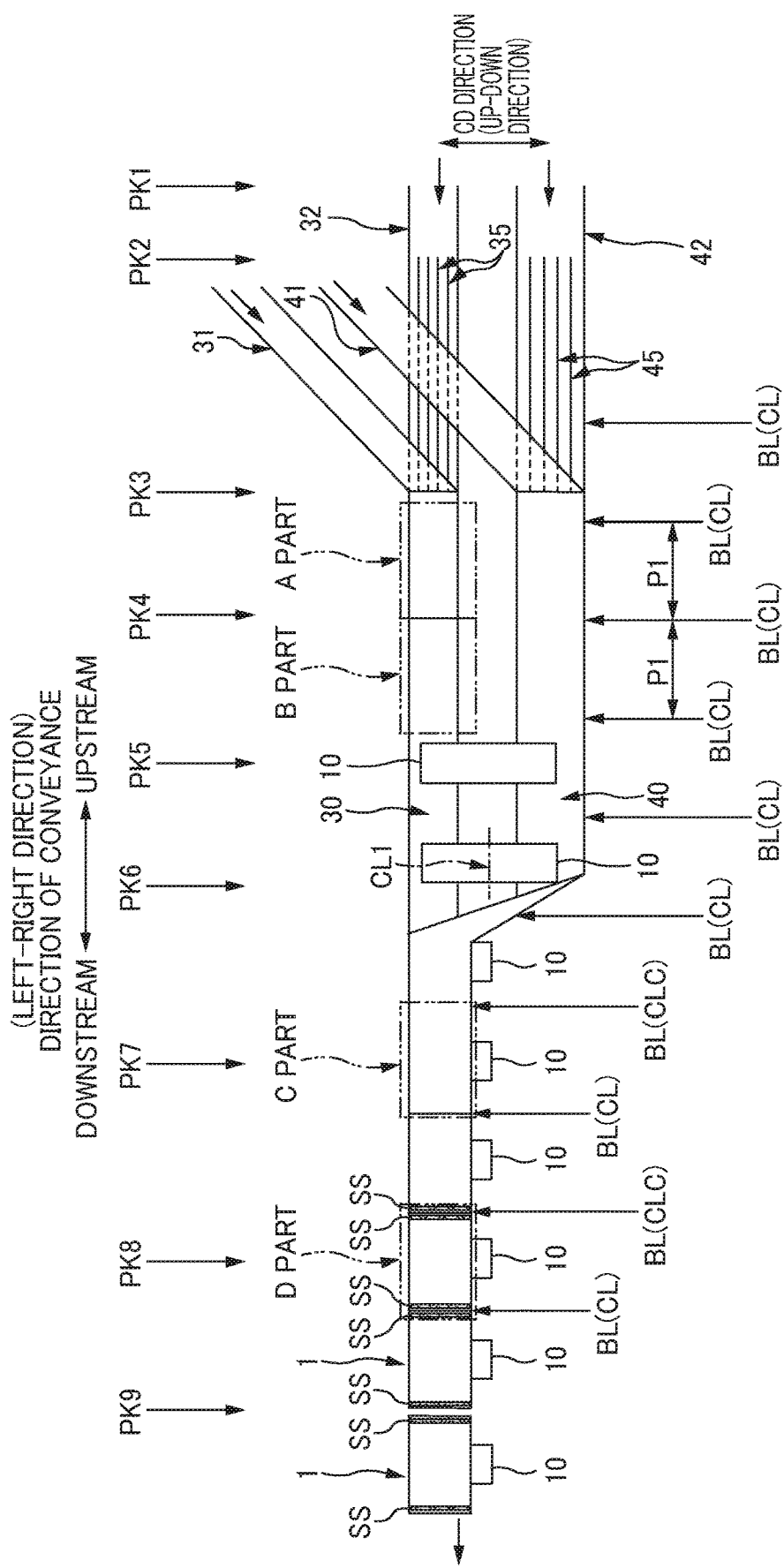
FIG. 7 is a partially perspective schematic plan view illustrating the diaper 1 manufactured on a production line according to one or more embodiments.
Figure 8A:
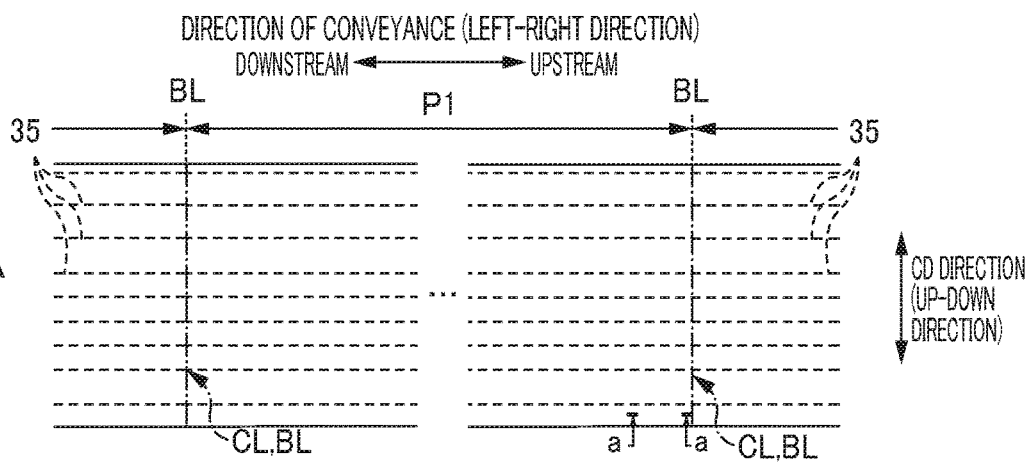
FIG. 8A is a schematic enlarged view illustrating a part A in FIG. 7.
Figure 8B:
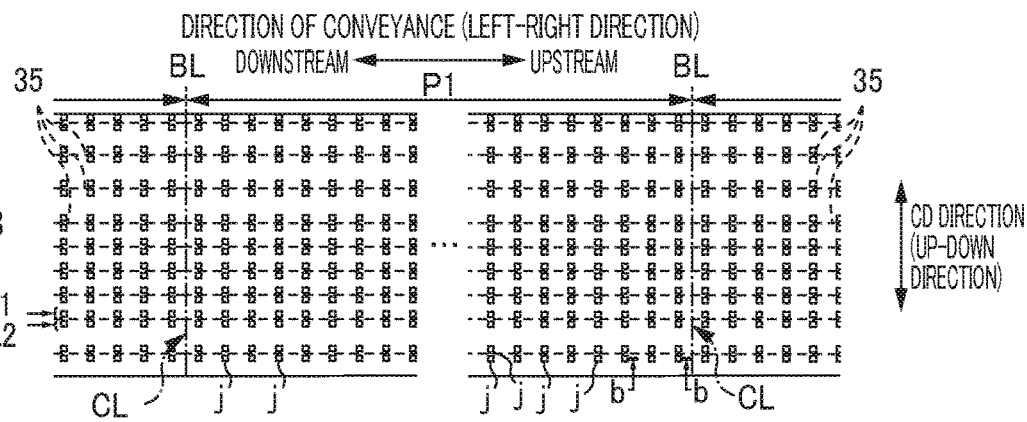
FIG. 8B is a schematic enlarged view illustrating a part B in FIG. 7.
Figure 8C:
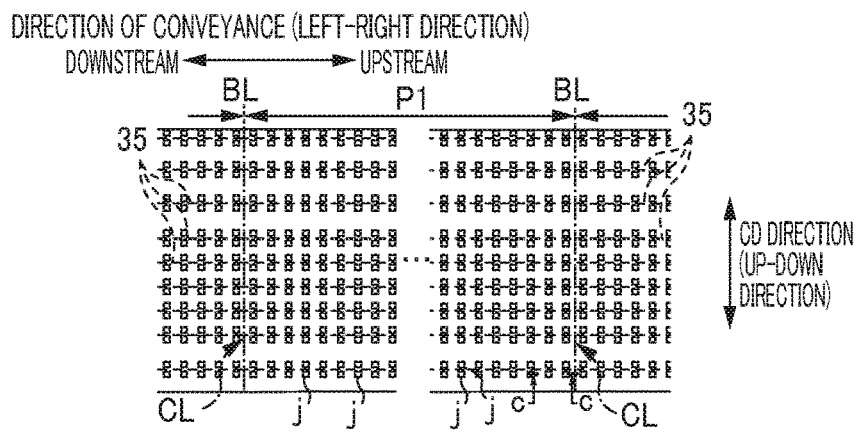
FIG. 8C is a schematic enlarged view illustrating a part C in FIG. 7.
Figure 8D:
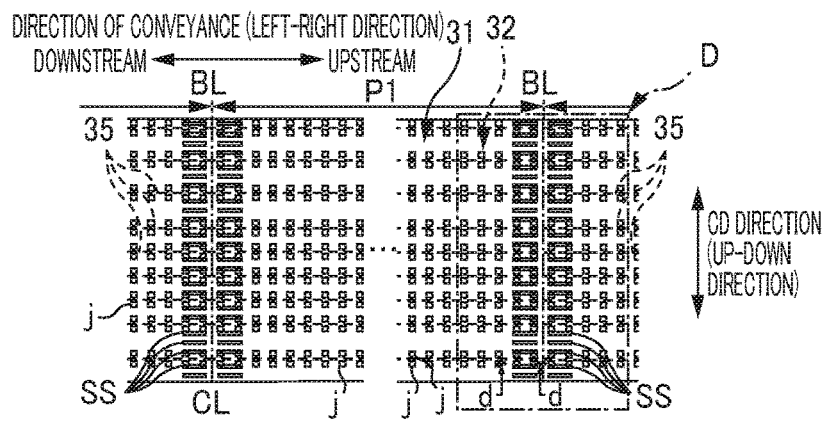
FIG. 8D is a schematic enlarged view illustrating a part D in FIG. 7.

A method for manufacturing the diaper 1 will hereinafter be described. FIG. 6 is a flowchart illustrating a manufacturing process of the diaper 1. FIG. 7 is a partially perspective schematic plan view illustrating the diaper 1 manufactured on a production line. FIG. 8A is a schematic enlarged view illustrating a part A in FIG. 7. FIG. 8B is a schematic enlarged view illustrating a part B in FIG. 7. FIG. 8C is a schematic enlarged view illustrating a part C in FIG. 7. FIG. 8D is a schematic enlarged view illustrating a part D in FIG. 7. FIG. 9A is a schematic diagram for describing a cross section taken along the line a-a of FIG. 8A. FIG. 9B is a schematic diagram for describing a cross section taken along the line b-b of FIG. 8B. FIG. 9C is a schematic diagram for describing a cross section taken along the line c-c of FIG. 8C. FIG. 9D is a schematic diagram for describing a cross section taken along the line d-d of FIG. 8D.

In FIG. 7 and the like, a direction orthogonal to the thickness direction and the direction of conveyance of the sheets 31, 32, 41, and 42 will be referred to as a "CD direction" or "up-down direction", and the direction of conveyance will be also referred to as a "left-right direction". Further, although the front member 30 will be described with reference to FIGS. 8A to 8D and 9A to 9C in the following description, this description may also apply to the back member 40. In FIGS. 7 and 8A to 8D, a product pitch P1 is virtually set in the direction of conveyance as boundary positions BL each between the diapers 1 continuous in the left-right direction. CL refers to a cutting position CL for cutting the diaper 1 at the boundary position BL, as a cutting target position, in the ninth processing position PK9 located in the end of the production line. Further, the cross-sectional view of FIG. 9A taken along the line a-a of FIG. 8A, the cross-sectional view of FIG. 9B taken along the line b-b of FIG. 8B, and the cross-sectional view of FIG. 9C taken along the line c-c of FIG. 8C illustrate cross sections of the front member 30 of the diaper 1. The cross-sectional view of FIG. 9D taken along the line d-d of FIG. 8D illustrates the same parts in the cross sections of the front member 30 and the back member 40 of the diaper 1.

As illustrated in FIG. 6, the front member 30 is formed by performing a non-skin-side sheet conveyance process S301, an elastic string placing process S302, a skin-side sheet placing process S303, and a sheet member welding process S304. Further, the back member 40 is formed by performing a non-skin-side sheet conveyance process S401, an elastic string placing process S402, a skin-side sheet placing process S403, and a sheet welding process S404. Then, the diaper 1 is formed by performing an absorbent main body placing process S505, an overlapping process S506, a releasing process S507, a side welding process S508, and a cutting process S509.

Each of the processes will hereinafter be described with reference to FIG. 7. Note that the members (including the skin-side sheets 31 and 41, the non-skin-side sheets 32 and 42, the elastic strings 35 and 45, and the diaper 1) continue along the direction of conveyance in the processes until the diaper 1 is individually cut out in the cutting process S508.

First, the non-skin-side sheet conveyance process S301, S401 is performed at the first processing position PK1. Specifically, the non-skin-side sheets 32 and 42 continuing along the direction of conveyance are individually conveyed downstream in the direction of conveyance using a conveying device such as a conveying roller (not shown).

Then, the elastic string placing process (S302, S402) is performed at the second processing position PK2. In the elastic string placing process, a plurality of elastic strings 35 and 45 continuing along the direction of conveyance is placed at predetermined intervals in the CD direction from the upper side in the thickness direction of the conveyed non-skin-side sheet 32, 42. The placement of the elastic strings is performed using a conveying device (an elastic member placing unit) such as a conveying roller (not shown). In the elastic string placing process, the elastic strings 35 and 45 are stretched at a predetermined stretch rate.

The stretch rate is referred to as R (P=E1/E0) indicating how many times a total length E1 of each of the string 35, 45 is stretched relative to a natural total length E0 without load (natural state). In addition, a predetermined stretch rate R according to one or more embodiments may be selected from a range of, for example, 1.5 to 4.0. According to one or more embodiments, the stretch rate is set to 2.0 (R=2.0).

Subsequently, the skin-side sheet placing process S303, S403 is performed at the third processing position PK3. In the skin-side sheet placing process, the skin-side sheets 31 and 41 are placed from the upper side in the thickness direction of the non-skin-side sheets 32 and 42, respectively, where the elastic strings 35 and 45 are arranged. As a result, as illustrated in FIG. 8A, in the part A after the non-skin-side sheet placing process S303, S403, the stretched elastic string 35 is interposed between the skin-side sheet 31 and the non-skin-side sheet 32. Then, the diaper 1 is conveyed downstream in the direction of conveyance.

In this case, as illustrated in FIG. 9A, the elastic string 35 (45) is thinned as much as the elastic string 35 (45) in the natural state is stretched. Further, since the skin-side sheet 31 (41) and the non-skin-side sheet 32 (42) are conveyed so as to be pulled from the downstream side in the direction of conveyance, they are conveyed while being applied with an appropriate tension.

Subsequently, the sheet member welding process S304, S404 is performed at the fourth processing position PK4. In FIG. 7, the part B represents a state after the sheet member welding process. In the sheet member welding process, the skin-side sheet 31 and the non-skin-side sheet are welded with a plurality of sheet weld portions j to form the front member 30 and the back member 40. The sheet weld portions j are arranged at intervals from one end portion to another end portion in the left-right direction in each of the front member 30 and the back member 40, that is, from a region of the cutting position CL on the downstream side to a region of the cutting position CL on the upstream side in the direction of conveyance. In the part B after the sheet member welding process, the sheet weld portions j having a substantially rectangular shape are arranged such that a plurality of weld lines L arranged side by side along the direction of conveyance is arranged along the CD direction while the sheet weld portions j adjacent to each other in the direction of conveyance are spaced apart at intervals as illustrated in FIG. 8B.

As recognized from the cross-sectional structure of FIG. 9B, the skin-side sheet 31 (41) and the non-skin-side sheet 32 (42) are integrated by welding and bonding the skin-side sheet 31 (41) and the non-skin-side sheet 32 (42). Note that, in the sheet member welding process as well, the elastic strings 35 (45) are conveyed in a stretched state so that they become thinner than the elastic strings 35 (45) in the natural state. Further, the sheet members 31 and 32 (41 and 42) are conveyed while being applied with an appropriate tension.

A plurality of sheet weld portions j is used not only to bond the skin-side sheet 31, 41 and the non-skin-side sheet 32, 42, respectively, but to mount the elastic strings 35, 45. The intervals (predetermined intervals) Dj of the sheet weld portions j located on both sides in the CD direction (see FIG. 10) to sandwich the elastic string 35 are at substantially regular intervals. Each of the intervals Dj is greater than the length of the elastic string 35 in the CD direction that is stretched to a predetermined stretch rate at the first processing position PK1, and is smaller than the natural length of the elastic string 35 in the CD direction without load. Accordingly, as the elastic string 35 approaches its natural state, the elastic string 35 is thickened, so that the elastic string 35 can be restricted with the sheet weld portions j being pressed in the up-down direction. In this manner, by fixing the elastic string 35 to the sheet weld portions j using stretch or contraction, it is possible to reduce the amount of the adhesive used to fix the elastic string 35 or not to use the adhesive, thereby being able to further softening the front member 30 and improving the texture.

The sheet weld portions j may be formed using an ultrasonic welding device (not shown). The ultrasonic welding device includes, for example, a horn having a vibration surface to vibrate in a normal direction and an anvil roll to rotate in the direction of conveyance. The anvil roll has a recess corresponding to each side weld portion SS on its outer peripheral surface to receive this vibration surface.

Then, the absorbent main body placing process S505 is performed at the fifth processing position PK5. In the absorbent main body placing process, a single-cut type absorbent main body 10 formed by a separate process (not shown) is stretched between the front member 30 and the back member 40 and fixed thereto. When the absorbent main body 10 is fixed, a continuous body of the diaper 1 having a substantially ladder shape is formed along with the front member 30 and the back member 40. The placement of the absorbent main body 10 may be performed, for example, using a rotational drum device (not shown). The rotational drum device includes a rotatable drum that rotates along the direction of conveyance, and the rotatable drum has a plurality of holding portions for detachably holding the absorbent main body 10 on its outer peripheral surface. In the absorbent main body placing process, the elastic string 35 (45) are conveyed in a stretched state, and the sheet members 31 and 32 (41 and 42) are conveyed while being applied with an appropriate tension.

The overlapping process S506 is performed at the sixth processing position PK6. In the overlapping process, the absorbent main body 10 is folded in half at a predetermined position CL1 (see FIG. 2A) in the CD direction of the absorbent main body 10. As a result, the skin-side and non-skin-side sheets 31 and 32 of the front member 30 and the skin-side and non-skin-side sheets 41 and 42 of the back member 40 are overlapped in the thickness direction. In the overlapping process, the elastic strings 35 (45) are conveyed in a stretched state, and the sheet members 31 and 32 (41 and 42) are conveyed while being applied with an appropriate tension.

The overlapping process may be performed, for example, using a folding guide device (overlapping unit) (not shown). The folding guide device includes a guide plate or a guide roller disposed at a predetermined position in the direction of conveyance. Then, the guide plate or the guide roller guides a continuous body of the diapers 1 in a substantially ladder shape passing through the placement position so as to form a double folded shape.

Subsequently, the releasing process S507 is performed at the seventh processing position PK7. In the releasing process, the stretched state of the elastic strings 35, 45 are loosened to release the stretch. In the part C (FIG. 8C), a state after the releasing process is illustrated. The released state obtained by releasing the stretch of the elastic strings 35, 45 refers to a state between the stretched state and the natural state of the elastic strings 35 (45). According to one or more embodiments, the released state refers to a state in which the elastic strings 35, 45 contract until the length of the elastic strings 35 (45) is reduced to 50% to 70% in their stretched state in the elastic string placing process S302 or S402. The releasing process may be performed, for example, using a speed-change conveying device (releasing unit) including a conveying roller (not shown) and/or the like. The speed-change conveying device includes a plurality of conveying rollers. At the seventh processing position PK7, a first roller conveys the diapers at a substantially constant speed from the non-skin-side sheet member placement process S301 to the overlapping process S506, and a second roller that rotates slower than the first roller is used to convey the diapers in a region downstream of the part C. By adjusting rotation speeds of the first roller and the second roller, it is possible to adjust the degree of releasing of the elastic strings 35 (45) and/or wrinkles formed in the skin-side sheet 31 (41) and/or the non-skin-side sheet 32 (42).

FIG. 8C illustrates a part C in which the stretch of the elastic strings 35 and 45 is loosened. As illustrated in FIG. 8C, by releasing the stretch of the elastic strings 35, the elastic strings 35 contract in the direction of conveyance. According to one or more embodiments, the elastic strings 35 (45) are caused to contract until the length thereof reaches 60% of the length in the stretched state in the elastic string placing process S302 or the like, as well as the elastic strings 35 (45) are stretched to be longer than the natural length of the elastic strings 35 (45). In this manner, in the releasing process and the subsequent processes of one or more embodiments, the elastic strings 35 (45) are released in a state between the stretched state of the elastic string placing process S302 or the like and the natural length at no load, without being stretched to the natural length. As the elastic strings 35 (45) are loosened to the natural length, the positioning on the production line becomes difficult, so that the welding process S508 and the cutting process S509 described below may not be performed at the accurate positions. Accordingly, the elastic strings 35 are appropriately stretched in a suitably loosened state, thereby being able to perform processing at more accurate positions in the downstream processes.

Note that the region of the front member 30 illustrated in FIG. 8C is the same region as that illustrated in FIGS. 8A and 8B. That is, the pitch P1 of FIG. 8C results in 60% of the pitch P1 in the elastic string placing process S302 of FIG. 8A and the sheet member welding process S304 of FIG. 8B due to contraction of the elastic string 35. For convenience, FIGS. 8A to 8D illustrate the diapers 1 being aligned on the right side (upstream side in the direction of conveyance), and FIGS. 8C and 8D illustrate a state of the diapers 1 continuing along the direction of conveyance while omitting the left side (downstream side in the direction of conveyance).

In this case, the elastic string 35 of the front member 30 (or the elastic string 45 of the back member 40) is shorter in the direction of conveyance than that in the stretched state, and is thicker in the up-down direction and the thickness direction. Furthermore, the sheet members 31 and 32 (41 and 42) are loosened such that parts of the skin-side sheet 31 (41) and the non-skin-side sheet 32 (42) excluding the sheet weld portions j protrude toward the skin side and the non-skin side, respectively. That is, in the skin-side sheet 31 (41) and the non-skin-side sheet 32 (42), at least one wrinkle is formed into projection or depression in the up-down direction between the sheet weld portions j adjacent to each other in the direction of conveyance, thereby forming a plurality of wrinkles in the direction of conveyance in the region illustrated in FIG. 8C.

As illustrated in FIG. 9C, when wrinkles are formed in the skin-side sheet 31 (41) and the non-skin-side sheet 32 (42) by releasing stretch of the elastic string 35 (45), the basis weight of the nonwoven fabric of the skin-side sheet 31 (41) and the non-skin-side sheet 32 (42) (the weight of the nonwoven fabric per unit area) increases. That is, the amount (the weight) of the nonwoven fabric of the skin-side sheet 31 (41) and the non-skin-side sheet 32 (42) in FIG. 9B is equal to the amount (the weight) of the nonwoven fabric of the skin-side sheet 31 (41) and the non-skin-side sheet 32 (42) in FIG. 9C. However, after the releasing process of FIG. 9C, the area is reduced with the contraction of the elastic string 35 (45), so that the amount of the nonwoven fabric per unit area increases.

Then, the side welding process S508 is performed at the eighth processing position PK8. In the welding process, the skin and non-skin-side sheets 31 and 32 of the front member 30 and the skin and non-skin-side sheets 41 and 42 of the back member 40 overlapping in the thickness direction are welded on both sides of the cutting position CL to form a pair of side weld portions SS, while maintaining the released state in which stretch of the elastic strings 35 and 45 are released through the releasing process. The front member 30 and the back member 40 are welded with the side weld portions SS being formed. A plurality of side weld portions SS having substantially the same shape is arranged side by side at intervals along the CD direction in a rectangular shape elongated in the left-right direction.

The side weld portions SS may be formed, for example, using an ultrasonic welding device (a weld forming unit) (not shown). The ultrasonic welding device includes, for example, a horn having a vibration surface to vibrate in a normal direction and an anvil roll to rotate in the direction of conveyance. The anvil roll has a recess corresponding to each side weld portion SS on its outer peripheral surface to receive this vibration surface.

FIG. 8D illustrates a part D in which the side weld portions SS are formed in a state where stretch of the elastic string 35 is loosened. As illustrated in FIG. 8D, a plurality of side weld portions SS for welding the end portions on the downstream side of each of the front member 30 and the back member 40 and welding the end portions on the upstream side of each of the front member 30 and the back member 40 is provided, on both sides of the cutting position CL, at intervals in the CD direction, while stretch of the elastic strings 35 and 45 of FIG. 8C is loosened.

As illustrated in FIG. 9D, the skin-side sheets 31 and 41 and the non-skin-side sheets 32 and 42 having the wrinkles having projections and depressions in the up-down direction formed in the releasing process (FIGS. 8C and 9C) are squeezed in the thickness direction as the side weld portions SS are formed, so that the sheets become substantially in parallel in the direction of conveyance. Since the side welding process is performed while stretch/contraction of the elastic strings 35 and 45 is released, the basis weight of the nonwoven fabric of each of the front member 30 and the back member 40 increases by virtue of contraction of the elastic strings 35 and 45, as compared to the basis weight in the state where the elastic strings 35 and 45 are stretched. As a result, the welding strength increases more in a case where the front member 30 and the back member 40 are welded to each other in a state where the elastic strings 35 and 45 are in the released state, than the welding strength in a case where the front member 30 and the back member 40 are welded and bonded to each other in a state where the elastic strings 35 and 45 are in a stretched state. This is because the welding and bonding is a process of melting nonwoven fabrics and bonding the melted nonwoven fabrics to each other. Thus, as the amount of nonwoven fabric increases more, the bonding strength is improved more. Accordingly, it is possible to reduce the possibility that bonding of the end portions (side ends 30a and 40a) in the left-right direction of the front member 30 and the back member 40 is broken when putting on the pull-on disposable diaper 1 of FIG. 1 or when the diaper 1 is worn.

It is also possible to improve the welding strength between the front member 30 and the back member 40, even when the basis weight of the nonwoven fabric of the front member 30 and the back member 40 is reduced in order to improve breathability of the front member 30 and the back member 40, reduce costs, or improve texture. That is, since the side weld portions SS are formed while wrinkles are formed in the front member 30 and the back member 40 by releasing stretch of the elastic strings 35 and 45 through the releasing process, it is possible to increase the basis weight of the nonwoven fabrics of the front member 30 and the back member 40 in the side weld portions SS by virtue of the wrinkles even when the basis weight of the nonwoven fabrics of the front member 30 and the back member 40 is small. Accordingly, it is possible to improve the strength of the side weld portion SS.

Figure 10:
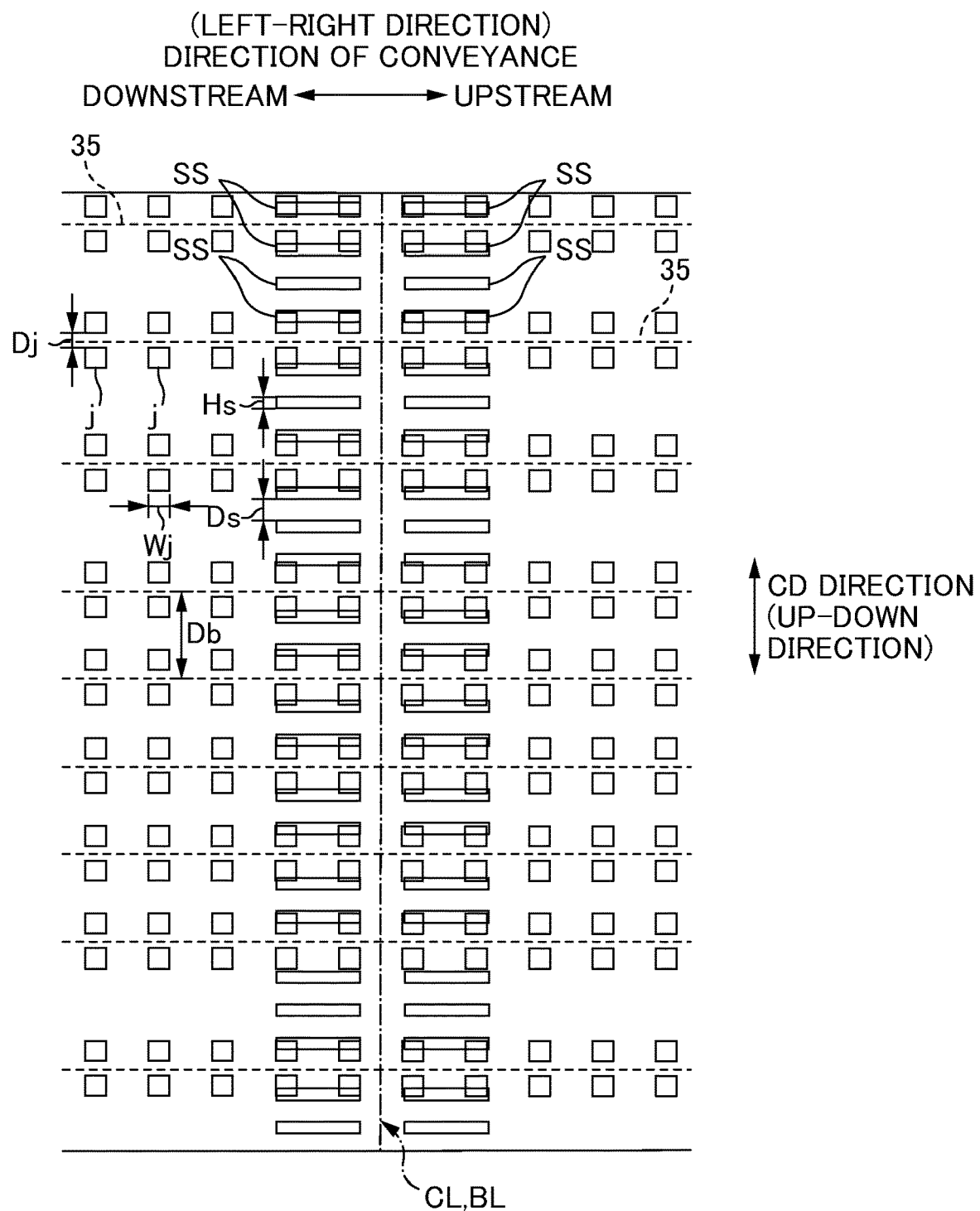
FIG. 10 is a schematic enlarged view illustrating a region D of FIG. 8D.

As illustrated in FIG. 10, in one or more embodiments, the side weld portion SS is formed in a position overlapping with at least one sheet weld portion j in the thickness direction. In one or more embodiments, the side weld portion SS is formed so as to overlap with two or more sheet weld portions j in the thickness direction. As described above, wrinkles are formed between the sheet weld portions j adjacent to each other in the direction of conveyance by releasing the elastic strings 35 and 45. When the side weld portion SS is formed on at least one sheet weld portion j, at least a part of wrinkles between the sheet weld portions j is likely to be formed into a crushed shape. In addition, with provision of the side weld portion SS overlapping with two or more sheet weld portions j in the thickness direction, it is possible to more reliably crush wrinkles between the sheet weld portions j. As a result, the basis weights of the nonwoven fabrics of the front member 30 and the back member 40 increase in the side weld portions SS, thereby being able to improve the welding strength of the side weld portions SS.

As illustrated in FIG. 10, in one or more embodiments, the interval Ds of the side weld portions SS adjacent to each other in the up-down direction is greater than the interval Dj of the sheet weld portions j adjacent to each other in the up-down direction (Ds>Dj). Since the elastic string 35, 45 are placed between the sheet weld portions j adjacent each in the up-down direction, it is possible to reduce the possibility that the elastic string 35, 45 is broken when the side weld portions SS are formed, as compared to a case where the interval Ds of the side weld portions SS adjacent to each other in the up-down direction is smaller than the interval Dj of the sheet weld portions j adjacent to each other in the up-down direction.

A length Ws in the left-right direction of the side weld portion SS is greater than a length Wj in the left-right direction of the sheet weld portion j (Ws>Wj), in one or more embodiments. If the length Ws in the left-right direction of the side weld portion SS is smaller than the length Wj in the left-right direction of the sheet weld portion j (Ws<Wj), the side weld portion SS may be formed in a region overlapping with only the sheet weld portion j in the left-right direction. In this case, even when the stretch of the elastic strings 35 and 45 are released in the releasing process, it is difficult to perform welding such that the side weld portion SS crushes wrinkles, which makes it difficult to increase the basis weight of the nonwoven fabrics in the side weld portion SS. In this regard, if the length Ws in the left-right direction of the side weld portion SS is greater than the length Wj in the left-right direction of the sheet weld portion j (Ws>Wj), it is possible to easily crush the wrinkles provided outside in the left-right direction of the sheet weld portion j when the side weld portion SS is formed. Thus, it is possible to easily increase the basis weight of the nonwoven fabric in the side weld portion SS, thereby being able to improve the welding strength of the side weld portion SS.

Further, in one or more embodiments, the interval Db of the elastic strings 35 adjacent to each other in the up-down direction is greater than the length Hs in the up-down direction of the side weld portion SS (Db>Hs). Note that, when the intervals Db of the elastic strings 35 adjacent to each other in the up-down direction are not equal as illustrated in FIG. 10, the smallest interval Db of the elastic strings 35 is greater than a length Hs in the up-down direction of the side weld portion SS, in one or more embodiments. As a result, it is possible to reduce the possibility that the elastic string 35 is broken when the side weld portion SS is formed.

Finally, the cutting process S509 is performed at the ninth processing position PK9. In the cutting process, individual diapers 1 are formed by cutting the diapers 1 continuous in the direction of conveyance at the cutting position CL while stretch of the elastic strings 35 and 45 is released. In this cutting process, the skin-side sheets 31 and 41, the non-skin-side sheets 32 and 42, and the elastic strings 35 and 45 that are in a state of being continuous along the direction of conveyance are cut out at the respective cutting positions CL.

Similarly to the side welding process, the cutting process is performed while the stretch of the elastic strings 35 and 45 is released in the releasing process, in one or more embodiments. When the stretch of the elastic strings 35 and 45 is released, the elastic strings 35 and 45 are thickened, which bring about a state where the elastic strings 35 and 45 can easily be pressed, in the CD direction, between the sheet weld portions j and the side weld portions SS. By cutting the front member 30 and the back member 40 including the elastic strings 35 and 45 in a state of being fixed with the sheet weld portions j and the side weld portions SS, it is possible to more easily maintain the state where the elastic strings 35 and 45 are fixed with the sheet weld portions j, as compared to a case where the front and back members are cut out while the elastic strings 35 and 45 are stretched. Further, if the cutting process is performed in a state where the elastic strings 35 and 45 are stretched, the elastic strings 35 and 45 that are stretched thin in the up-down direction and the front-rear direction contracts with a strong force immediately after cutting, so that the elastic strings 35 and 45 fixed by the side weld portions SS and/or the sheet weld portions j may come off from the fixation with the side weld portions SS and/or the sheet weld portions j. In this regard, by performing the cutting process while stretch of the elastic strings 35 and 45 is released, it is possible to reduce a contracting force of the elastic strings 35 and 45, thereby being able to reduce the possibility that the elastic strings 35 and 45 of individual diapers 1 come off from the fixation of the side weld portions SS and/or the sheet weld portions j.

The cutting process may be performed, for example, using a cutter device (cutting unit) (not shown). The cutter device has a pair of rolls configured to rotate along the direction of conveyance. One of the rolls is a cutter roll having a cutter blade on its outer peripheral surface, and the other roll is an anvil roll configured to receive the cutter blade on the outer peripheral surface.

Note that, although each of the sheet weld portions j and the side weld portions SS has a rectangular shape in the cross-sectional views of FIGS. 9B, 9C, and 9D, they may not have a rectangular shape and their boundaries are ambiguous because the welded region gently changes in practice.

Other Examples

The above examples of one or more embodiments are simply to facilitate understanding of the present invention and are not in any way to be construed as limiting the present invention. The present invention may variously be changed or altered without departing from its gist and encompass equivalents thereof. For example, the following modifications may be possible.

In the aforementioned examples of one or more embodiments, the releasing process S507 is provided before the side weld portions SS where the front member 30 including the elastic string 35 and the back member 40 including the elastic string 45 are welded and bonded, and the side welding process S508 is performed while the elastic strings 35 and 45 are released. However, it is not limited thereto. The present invention may be applicable to bonding between one of the members (first member) including the elastic member and the other member (second member) including no elastic member.

Figure 11:
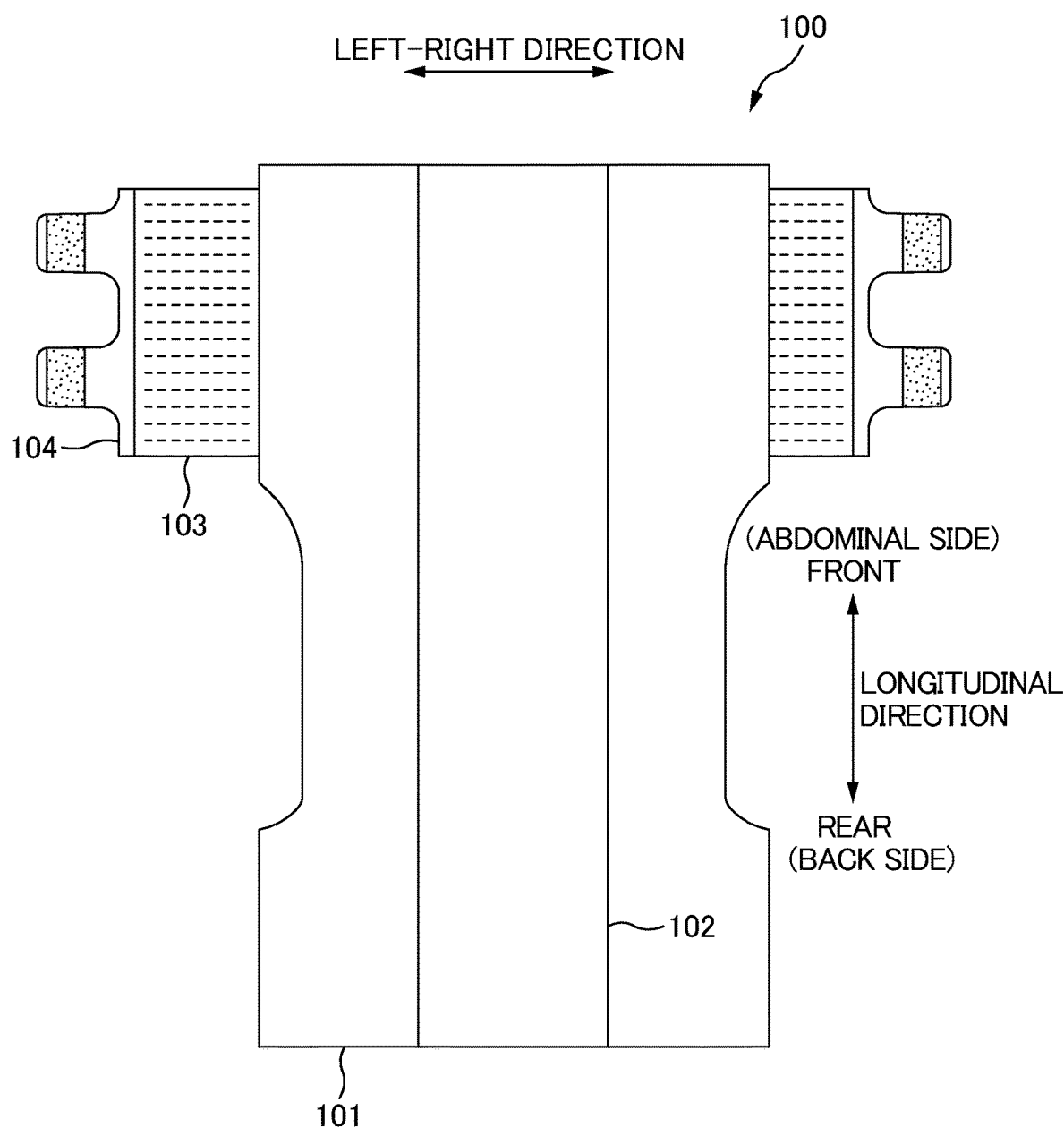
FIG. 11 is a diagram illustrating another example of one or more embodiments.

FIG. 11 is a diagram illustrating another example of one or more embodiments. The disposable diaper 100 of FIG. 11 is a tape-type diaper including an exterior sheet 101 and an absorbent body 102. The disposable diaper 100 also includes side panels 103, having elastic members, in one end portion in the longitudinal direction, the side panels 103 are provided outside the exterior sheet 101 in the left-right direction, and hook members 104 are respectively provided outside the side panels 103 in the left-right direction. Each of the side panels 103 and the hook members 104 includes a nonwoven fabric. The present invention may be applicable to a process of welding the hook member 104 to the side panel 103 in the manufacturing process of this diaper 100. Specifically, the stretched elastic member of the side panel 103 may be released before welding and bonding the hook member 104 to the side panel 103, and the side panel 103 and the hook member 104 may be welded and bonded in the released state. As a result, it is possible to further strengthen bonding between the side panel 103 and the hook member 104, thereby being able to further reduce the possibility that the hook member 104 comes off from the side panel 103 when a guardian or the like tries to put the diaper 100 on an infant or while an infant wears the diaper 100.

In the aforementioned examples of one or more embodiments, the releasing process S507 is provided between the overlapping process S506 and the side welding process S507, and the side weld portions SS are formed while the elastic strings 35 and 45 are released, so that the sum of the basis weight of the nonwoven fabric of the front member 30 and the basis weight of the nonwoven fabric of the back member 40 in the weld region E increases. However, the present invention is not limited thereto. For example, the sheet members 31, 32, 41, and 42, in which the basis weight of the nonwoven fabric increases in advance in the portions corresponding to the weld regions E of the front member 30 and the back member 40, may be used.

In the aforementioned examples of one or more embodiments, the basis weight of the nonwoven fabric in the portion corresponding to the weld region E of the front member 30 and the portion corresponding to the weld region E of the back member 40 is set to be greater than the basis weight of the nonwoven fabric in the portion corresponding to the adjacent region N of the front member 40 and the portion corresponding to the adjacent region E of the back member 40. However, the present invention is not limited thereto. For example, the basis weight of the nonwoven fabric of the weld region E in the front member 30 may be set to be greater than the basis weight of the nonwoven fabric of the adjacent region N in the front member 30, and the basis weight of the nonwoven fabric may be set to be equal between the adjacent region N and the weld region E of the back member 40. Since the side weld portions SS are bonded by melting the nonwoven fabric, it is possible to improve the strength of the side weld portions SS by increasing the sum of the basis weight of the nonwoven fabric of the front member 30 and the basis weight of the nonwoven fabric of the back member 40 in the weld region E, even when the basis weight of the nonwoven fabric is different between the front member 30 and the back member 40.

Note that, although elastic strings 35 and 45 are given as examples of the elastic members provided in the front member 30 and the back member 40 are in the aforementioned examples of one or more embodiments, it is not limited thereto. In place of the elastic strings, for example, a single or a plurality of sheet-like elastic members such as an elastic film or elastic nonwoven fabric may also be disposed.

Although the sheet weld portion j and the side weld portion SS are ultrasonically joined using an ultrasonic sealing device in the aforementioned examples of one or more embodiments, it is not limited thereto. Other welding methods may also be employed. For example, heat seal welding using a heat seal device including a pair of heated rolls may also be employed.

The sheet weld portion j and the side weld portion SS do not necessarily have a rectangular shape. The shapes are not limited to the rectangular shape, but other given shapes such as an elliptical shape, a circular shape, and a parallelogram shape may also be employed.

It is not necessary to dispose a plurality of side weld portions SS at intervals in the up-down direction. For example, a single side weld portion SS provided from the upper end to the lower end in each end portion in the left-right direction of the diaper 1 may be provided.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

1: diaper (pull-on disposable diaper, absorbent article),
10: absorbent main body, 10*ea*: end portion, 10*eb*: end portion,
11: absorbent body, 11*c*: absorbent core,
13: top sheet, 15: back sheet,
30: front member (first member), 30*a*: side portion (end portion),
31: skin-side sheet member (first sheet member),
32: non-skin-side sheet member (first sheet member),
35: elastic string (elastic member, first elastic member),
40: back member (second member), 40*a*: side portion (end portion),
41: skin-side sheet member (second sheet member),
42: non-skin-side sheet member (second sheet member),
45: elastic string (elastic member, second elastic member),
100: diaper (tape-type disposable diaper, absorbent article),
101: exterior sheet, 102: absorbent body, 103: side panel, 104: hook member,
J: sheet weld portion,
E: weld region, N: adjacent region,
L1, L2: weld line,
P1: pitch, BL: boundary position, CL: cutting position,
SS: side weld portion,
LH: leg opening, BH: waist opening

What is claimed is:

1. An absorbent article having an up-down direction, a left-right direction, and a thickness direction orthogonal to the up-down direction and the left-right direction, the absorbent article comprising:
a first sheet body that comprises:
two first sheets at least one of which comprises a first nonwoven fabric, and
a first elastic string that is stretchable and contractible in the left-right direction;
a second sheet body that comprises:
two second sheets at least one of which comprises a second nonwoven fabric, and
a second elastic string that is stretchable and contractible in the left-right direction; and
a first weld portion where a first end portion of the first sheet body and a second end portion of the second sheet body are welded and bonded to each other, wherein the first end portion and the second end portion are positioned on a same side in the left-right direction, the absorbent article further comprises on each side in the left-right direction:
- a weld region that overlaps with the first weld portion and extends between upper and lower ends of the first and second sheet bodies; and
- an adjacent region that does not overlap with the first weld portion, extends between the upper and lower ends of the first and second sheet bodies, and is adjacent to the weld region from an inner side in the left-right direction, the first and second sheet bodies are welded within the weld region in a released state between a natural state and a stretched state in which the first and second sheet bodies are stretched along the left-right direction, a sum of basis weights of the first and second nonwoven fabrics in the weld region is greater than a sum of basis weights of the first and second nonwoven fabrics in the adjacent region, the sum in the weld region and the sum in the adjacent region are measured in the stretched state, and the sum in the weld region in the case where the first and second sheet bodies are welded in the released state is greater than the sum in the weld region in a case where the first and second sheet bodies are welded in the stretched state.

2. The absorbent article according to claim 1, wherein the first sheets are welded to each other at a plurality of second weld portions, the plurality of second weld portions is arranged at intervals from one end portion to another end portion of the first sheets in the left-right direction, a plurality of weld lines is disposed along the left-right direction while being spaced apart at a predetermined interval in the up-down direction, the first elastic string is disposed between the weld lines adjacent to each other in the up-down direction, and the predetermined interval is greater than a thickness of the first elastic string in the stretched state and is smaller than a thickness of the first elastic string in a natural state.

3. The absorbent article according to claim 2, wherein the first weld portion is disposed in a position overlapping with at least one of the plurality of second weld portions in the thickness direction.

4. The absorbent article according to claim 3, wherein the first weld portion is disposed in a position overlapping with two or more of the plurality of second weld portions in the thickness direction.

5. The absorbent article according to claim 3, further comprising:
a plurality of first weld portions disposed along the up-down direction, wherein an interval between the plurality of second weld portions that are adjacent to each other in the up-down direction with the first elastic string therebetween is closer than an interval between the plurality of first weld portions that are adjacent to each other in the up-down direction and do not have the first elastic string therebetween.

6. The absorbent article according to claim 3, wherein a length of the first weld portion in the left-right direction is greater than a length of each of the second weld portions in the left-right direction.

7. The absorbent article according to claim 3, wherein a plurality of first elastic strings including the first elastic string is disposed, a plurality of first weld portions including the first weld portion is disposed along the up-down direction, and an interval of the first elastic strings adjacent to each other in the up-down direction is greater than a length of each of the first weld portions in the up-down direction.

* * * * *